(12) United States Patent
Ojeda et al.

(10) Patent No.: US 11,883,181 B2
(45) Date of Patent: Jan. 30, 2024

(54) MULTIMODAL WEARABLE MEASUREMENT SYSTEMS AND METHODS

(71) Applicant: HI LLC, Los Angeles, CA (US)

(72) Inventors: Alejandro Ojeda, Culver City, CA (US); Ryan Field, Culver City, CA (US); Husam Katnani, Braintree, MA (US); Bruno Do Valle, Brighton, MA (US); Isai Olvera, San Jose, CA (US)

(73) Assignee: HI LLC, Los Angeles, CA (US)

( * ) Notice: Subject to any disclaimer, the term of this patent is extended or adjusted under 35 U.S.C. 154(b) by 80 days.

(21) Appl. No.: 17/176,309

(22) Filed: Feb. 16, 2021

(65) Prior Publication Data

US 2021/0259614 A1 Aug. 26, 2021

Related U.S. Application Data

(60) Provisional application No. 63/079,194, filed on Sep. 16, 2020, provisional application No. 63/006,824, filed on Apr. 8, 2020, provisional application No. 62/979,866, filed on Feb. 21, 2020.

(51) Int. Cl.
| | |
|---|---|
| *A61B 5/291* | (2021.01) |
| *A61B 5/369* | (2021.01) |
| *A61B 5/00* | (2006.01) |

(52) U.S. Cl.
CPC ............ *A61B 5/369* (2021.01); *A61B 5/0075* (2013.01); *A61B 5/291* (2021.01); *A61B 5/6803* (2013.01)

(58) Field of Classification Search
None
See application file for complete search history.

(56) References Cited

U.S. PATENT DOCUMENTS

| | | | |
|---|---|---|---|
| 4,018,534 A | 4/1977 | Thorn et al. | |
| 4,207,892 A | 6/1980 | Binder | |
| 4,281,645 A | 8/1981 | Jobsis | |
| 4,321,930 A | 3/1982 | Jobsis | |
| 4,515,165 A | 5/1985 | Carroll | |

(Continued)

FOREIGN PATENT DOCUMENTS

| | | |
|---|---|---|
| CN | 200950235 | 9/2007 |
| CN | 107865635 | 4/2018 |

(Continued)

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680.

(Continued)

*Primary Examiner* — Alex M Valvis
*Assistant Examiner* — Aurelie H Tu
(74) *Attorney, Agent, or Firm* — ALG Intellectual Property, LLC

(57) ABSTRACT

An illustrative multimodal measurement system includes a wearable assembly configured to be worn by a user and comprising a plurality of light sources each configured to emit light directed at a target within the user, a plurality of detectors configured to detect arrival times for photons of the light after the light is scattered by the target, and a plurality of electrodes configured to be external to the user and detect electrical activity of the target.

18 Claims, 21 Drawing Sheets

(56) References Cited

U.S. PATENT DOCUMENTS

| | | |
|---|---|---|
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,240,309 B1 | 5/2001 | Yamashita et al. |
| 6,291,824 B1 | 9/2001 | Battarbee et al. |
| 6,384,663 B2 | 5/2002 | Cova et al. |
| 6,541,752 B2 | 4/2003 | Zappa et al. |
| 6,618,614 B1 | 9/2003 | Chance |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,634,826 B1 | 4/2017 | Park |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 9,997,551 B2 | 6/2018 | Mandai et al. |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |
| 10,515,993 B2 | 12/2019 | Field et al. |
| 10,533,893 B2 | 1/2020 | Leonardo |
| 10,541,660 B2 | 1/2020 | McKisson |
| 10,558,171 B2 | 2/2020 | Kondo |
| 10,594,306 B2 | 3/2020 | Dandin |
| 10,627,460 B2 | 4/2020 | Alford et al. |
| 10,695,167 B2 | 6/2020 | Van Heugten et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 11,137,283 B2 | 10/2021 | Balamurugan et al. |
| 11,630,310 B2 | 4/2023 | Seidman et al. |
| 2002/0195545 A1 | 12/2002 | Nishimura |
| 2004/0057478 A1 | 3/2004 | Saito |
| 2004/0078216 A1 | 4/2004 | Toto |
| 2004/0160996 A1 | 8/2004 | Giorgi et al. |
| 2005/0038344 A1 | 2/2005 | Chance |
| 2005/0061986 A1 | 3/2005 | Kardynal et al. |
| 2005/0124863 A1 | 6/2005 | Cook |

(56) References Cited

U.S. PATENT DOCUMENTS

| | | |
|---|---|---|
| 2005/0228291 A1 | 10/2005 | Chance |
| 2006/0171845 A1 | 8/2006 | Martin |
| 2006/0197452 A1 | 9/2006 | Zhang |
| 2006/0264722 A1 | 11/2006 | Hannula et al. |
| 2007/0038116 A1 | 2/2007 | Yamanaka |
| 2007/0083097 A1 | 4/2007 | Fujiwara |
| 2008/0021341 A1* | 1/2008 | Harris .................. A61B 5/386 600/544 |
| 2009/0012402 A1 | 1/2009 | Mintz |
| 2009/0054789 A1* | 2/2009 | Kiguchi ............ A61B 5/0059 600/476 |
| 2009/0163775 A1 | 6/2009 | Barrett |
| 2009/0313048 A1 | 12/2009 | Kahn et al. |
| 2010/0188649 A1 | 7/2010 | Prahl et al. |
| 2010/0210952 A1 | 8/2010 | Taira et al. |
| 2010/0249557 A1 | 9/2010 | Besko et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1* | 4/2012 | Al-Ali .................. A61B 5/374 600/301 |
| 2012/0101838 A1 | 4/2012 | Lingard et al. |
| 2013/0015331 A1 | 1/2013 | Birk |
| 2013/0030267 A1 | 1/2013 | Lisogurski |
| 2013/0030270 A1* | 1/2013 | Chiou .................. A61B 5/369 600/344 |
| 2013/0032713 A1 | 2/2013 | Barbi et al. |
| 2013/0090541 A1 | 4/2013 | MacFarlane et al. |
| 2013/0144644 A1 | 6/2013 | Simpson |
| 2013/0221221 A1 | 8/2013 | Bouzid et al. |
| 2013/0225953 A1* | 8/2013 | Oliviero ............ A61B 5/0075 607/45 |
| 2013/0342835 A1 | 12/2013 | Blacksberg |
| 2014/0027607 A1 | 1/2014 | Mordarski et al. |
| 2014/0028211 A1 | 1/2014 | Imam |
| 2014/0055181 A1 | 2/2014 | Chavpas |
| 2014/0066783 A1 | 3/2014 | Kiani |
| 2014/0171757 A1* | 6/2014 | Kawato .................. A61B 5/377 600/545 |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0201841 A1 | 7/2015 | Ishikawa et al. |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0085547 A1* | 3/2017 | De Aguiar ............ H04L 63/10 |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1 | 6/2017 | Soulet De Brugere |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1* | 1/2018 | Chou .................. A61B 5/6803 |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1 | 5/2018 | Kuzniecky |
| 2018/0120152 A1 | 5/2018 | Leonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0025406 A1 | 1/2019 | Krelboim et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1* | 6/2019 | Everdell ............ A61B 5/0002 |
| 2019/0192031 A1 | 6/2019 | Laszlo et al. |
| 2019/0200888 A1 | 7/2019 | Poltorak |
| 2019/0209012 A1 | 7/2019 | Yoshimoto et al. |
| 2019/0261869 A1 | 8/2019 | Franceschini |
| 2019/0298158 A1 | 10/2019 | Dhaliwal |

(56) References Cited

U.S. PATENT DOCUMENTS

| | | |
|---|---|---|
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1 | 1/2020 | Vanegas |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0060542 A1 | 2/2020 | Alford |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson et al. |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

Bellis, Stephen et al., "Photon counting imaging: the DigitalAPD," Society of Photo-Optical Instrumentation Engineers (SPIE) Conference Series, Feb. 2006, vol. 6068, pp. 111-120.

Blutman, et al., "A 0.1 pJ Freeze Vernier Time-to-Digital Converter in 65nm CMOS," 2014 International Symposium on Circuits and Systems (ISCAS), Melbourne, Australia.

Cambie, Dario et al., "Every photon counts: understanding and optimizing photon paths in luminescent solar concentrator-based photomicroreactors (LSC-PMs)," React. Chem. Eng., 2017, 2, 561-566.

Contini, et al., "Photon migration through a turbid slab described by a model based on diffusion approximation. I. Theory," Appl. Opt. 36(19), 4587 (1997).

Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010 ,2010 ,1023-1030.

Dalla Mora, et al., "Memory effect in silicon time-gated single-photon avalanche diodes," http://dx.doi.org/10.1063/1.4915332, Journal of Applied Physics 117, 114501, 2015 ,2015 , 1-7.

De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487.

Di Sieno, et al., "Probe-hosted large area silicon photomultiplier and high-throughput timing electronics for enhanced performance time-domain functional near-infrared spectroscopy," Biomed. Opt. Express 11(11), 6389 (2020).

Dutton, et al., "A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5.

Fishburn, et al., "Temporal Derivative Distribution Repair (TDDR): A motion correction method for fNIRS," Neuroimage. Jan. 1, 2019; 184: 171-179. doi:10.1016/j.neuroimage.2018.09.025.

Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al., "Progress in Quenching Circuits for Single Photon Avalanche Diodes," IEEE Transactions on Nuclear Science, vol. 57, No. 6, Dec. 2010.

Gnecchi, et al., "A 1×16 SIPM Array for Automotive 3D Imaging LIDAR Systems."

Harmon, Eric S. et al., "Compound Semiconductor SPAD Arrays, LightSpin Technologies," http://www.lightspintech.com/publications.html.

Henderson, et al., "A 192×128 Time Correlated SPAD Image Sensor in 40-nm CMOS Technology," IEEE Journal of Solid-State Circuits, IEEE Journal of Solid-State Circuits, 2019.

Henderson, et al., "A 256×256 40nm/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.

Huppert, et al., "HomER: a review of time-series analysis methods for near-infrared spectroscopy of the brain," Appl. Opt. 48(10), D280 (2009).

Kienle, et al., "Improved solutions of the steady-state and the time-resolved diffusion equations for reflectance from a semi-infinite turbid medium," J. Opt. Soc. Am. A 14(1), 246 (1997).

Konugolu, et al., "Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring," Biomed. Opt. Express 11(10), 5934 (2020).

Lange, et al., "Clinical Brain Monitoring with Time Domain NIRS: A Review and Future Perspectives," Applied Sciences 9(8), 1612 (2019).

(56) References Cited

OTHER PUBLICATIONS

Lange, et al., "MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Lee, et al., "High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al., "A 4×4×416 digital SIPM array with 192 TDCs for multiple high-resolution timestamp acquisition," 2013 JINST 8 PO5024.

Martelli, et al., "Optimal estimation reconstruction of the optical properties of a two-layered tissue phantom from time-resolved single-distance measurements," Journal of Biomedical Optics 20(11), 115001 (Nov. 2015).

Maruyama, et al., "A 1024×8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014 ,2014 , 179-189.

Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.

Mora, et al., "Fast silicon photomultiplier improves signal harvesting and reduces complexity in time-domain diffuse optics," Opt. Express 23(11), 13937 (2015).

Mora,Alberto D. et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al., "A 256×256 SPAD array with in-pixel Time to Amplitude Conversion for Fluorescence Lifetime Imaging Microscopy," 2015.

Pifferi, et al., "Performance assessment of photon migration instruments: the MEDPHOT protocol," Applied Optics, 44(11), 2104-2114.

Prahl, et al., "Optical Absorption of Hemoglobin," http://omlc.ogi.edu/spectra/hemoglobin/index.html.

Puszka, et al.,"Time-resolved diffuse optical tomography using fast-gated single-photon avalanche diodes," Biomedical optics express, 2013, vol. 4, No. 8, pp. 1351-1365 (Year: 2013).

Re, et al.,"Multi-channel medical device for time domain functional near infrared spectroscopy based on wavelength space multiplexing," Biomed. Opt. Express 4(10), 2231 (2013).

Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).

Richardson, et al., "A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.

Takai, et al., "Single-Photon Avalanche Diode with Enhanced NIR-Sensitivity for Automotive LIDAR Systems," Sensors, 2016, 16(4): 459, pp. 1-9 (Year: 2016).

Torricelli, et al., "Time domain functional NIRS imaging for human brain mapping," NeuroImage 85, 28-50 (2014).

Wabnitz, et al., "Depth-selective data analysis for time-domain INIRS: moments vs. time windows," Biomed. Opt. Express 11(8), 4224 (2020).

Wabnitz, et al., "Performance assessment of time-domain optical brain imagers, part 1: basic instrumental performance protocol," Journal of Biomedical Optics 19(8), 086010 (Aug. 2014).

Wabnitz, et al., "Performance assessment of time-domain optical brain imagers, part 2: nEUROPt protocol," Journal of Biomedical Optics 19(8), 086012 (Aug. 2014).

Wojtkiewicz, et al., "Self-calibrating time-resolved near infrared spectroscopy," Biomed. Opt. Express 10(5), 2657 (2019).

Zhang, et al., "A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi: 10.3390/s18114016.

Zucchelli, et al., "Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.

International Search Report and Written Opinion received in International Application No. PCT/2020/027537, dated Sep. 7, 2020.

International Search Report and Written Opinion received in International Application No. PCT/2020/028820, dated Aug. 26, 2020.

International Search Report and Written Opinion received in International Application No. PCT/US20/34062, dated Aug. 26, 2020.

International Search Report and Written Opinion received in International Application No. PCT/US2018/058580, dated Feb. 12, 2019.

International Search Report and Written Opinion received in International Application No. PCT/US2018/062777, dated Feb. 13, 2019.

International Search Report and Written Opinion received in International Application No. PCT/US2019/019317, dated May 28, 2019.

Non-Final Office Action received in U.S. Appl. No. 16/177,351, dated Apr. 1, 2019.

Non-Final Office Action received in U.S. Appl. No. 16/283,730, dated May 16, 2019.

Non-Final Office Action received in U.S. Appl. No. 16/370,991, dated Feb. 10, 2020.

Non-Final Office Action received in U.S. Appl. No. 16/537,360, dated Feb. 25, 2020.

Non-Final Office Action received in U.S. Appl. No. 16/544,850, dated Jun. 25, 2020.

Non-Final Office Action received in U.S. Appl. No. 16/856,524, dated Dec. 1, 2020.

Partial Search Report received in International Application No. PCT/2020/028820, dated Jul. 1, 2020.

Partial Search Report received in International Application No. PCT/US2020/027537, dated Jul. 17, 2020.

"emojipedia.org", https://emojipedia.org (accessed May 27, 2021).

"International Search Report and Written Opinion received in International Application No. PCT/2021/018188".

"International Search Report and Written Opinion received in International Application No. PCT/US2021/018155".

"International Search Report and Written Opinion received in International Application No. PCT/US2021/018187".

"International Search Report and Written Opinion received in International Application No. PCT/US2021/018190".

"scienceofpeople.com/emojis", https://www.scienceofpeople.com/emojis/ (accessed May 27, 2021).

Hebert, et al., "Spatiotemporal image correlation spectroscopy (STICS) theory, verification, and application to protein velocity mapping in living CHO cells", Biophysical journal 88, No. 5 (2005): 3601-3614.

Kheng, et al., "Image Processing", https://www.comp.nus.edu.sg/~cs4243/lecture/imageproc.pdf, Mar. 9, 2014.

Sneha, et al., "Understanding Correlation", https://www.allaboutcircuits.com/technical-articles/understanding-correlation/, Jan. 4, 2017.

Xu, et al., "A 655 uW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.

Zucconi, et al., "The Autocorrelation Function", https://www.alanzucconi.com/2016/06/06/autocorrelation-function/, Jun. 6, 2016.

Chen, et al., "A PVT Insensitive Field Programmable Gate Array Time-to-digital Converter", 2013 IEEE Nordic-Mediterranean Workshop on Time-To-Digital Converters. Oct. 3, 2013.

Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.

(56) References Cited

OTHER PUBLICATIONS

Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.

Zheng, et al., "An Integrated Bias Voltage Control Method for SPAD Arrays", Oct. 1, 2018, IEEE Service Center.

Ahn, et al., "Multi-Modal Integration of EEG-fNIRS for Brain-Computer Interfaces—Current Limitations and Future Directions," Front. Hum. Neurosci. 11:503. doi: 10.3389/fnhum.2017.00503.

Croce, et al.,"Exploiting neurovascular coupling: a Bayesian sequential Monte Carlo approach applied to simulated EEG fNIRS data," J. Neural Eng. 14 (2017) 046029 (11pp).

Li, et al., "Dynamic cortical connectivity alterations associated with Alzheimer's disease: An EEG and fNIRS integration study," NeuroImage: Clinical 21 (2019) 101622; doi.org/10.1016/j.nicl.2018.101622.

Takeuchi, et al., "Brain Cortical Mapping by Simultaneous Recording of Functional Near Infrared Spectroscopy and Electroencephalograms from the Whole Brain During Right Median Nerve Stimulation," Brain Topography (2009) 22:197-214; DOI 10.1007/s10548-009-0109-2.

Tremblay, et al.,"Comparison of source localization techniques in diffuse optical tomography for fNIRS application using a realistic head model," vol. 9, No. 7 | Jul. 1, 2018 | Biomedical Optics Express 2994.

\* cited by examiner

MULTIMODAL WEARABLE MEASUREMENT SYSTEMS AND METHODS

RELATED APPLICATIONS

The present application claims priority under 35 U.S.C. § 119(e) to U.S. Provisional Patent Application No. 63/079,194, filed on Sep. 16, 2020, and to U.S. Provisional Patent Application No. 63/006,824, filed on Apr. 8, 2020, and to U.S. Provisional Patent Application No. 62/979,866, filed on Feb. 21, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
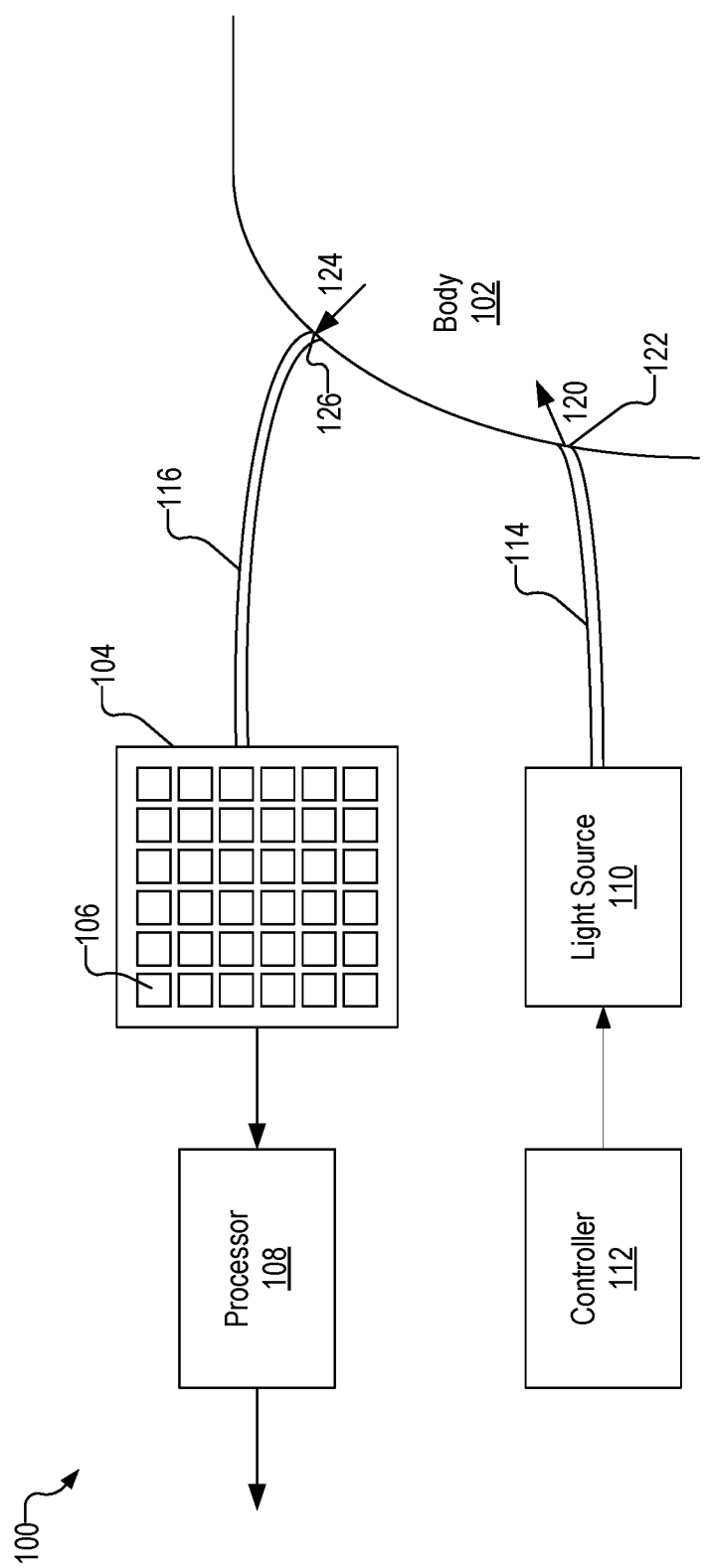
FIG. 1 illustrates an exemplary optical measurement system.

Functional near infrared spectroscopy (fNIRS) is a brain imaging modality that allows the indirect inference of cortical responses (a proxy for neural activity) by measuring the hemodynamic response of the brain tissue in different cortical regions. Compared to function magnetic resonance imaging (fMRI), another imaging modality based on the hemodynamic response, fNIRS can be mobile and low cost, allowing the large-scale use of imaging technology to study the brain, either within a tightly constrained environment of a scientific lab or in real-world scenarios, where subjects interact freely with their environment. One disadvantage of fNIRS, however, is that it is slow compared to the temporal dynamics of the current dipoles produced by neurons firing in the cortex. Another drawback of fNIRS is that there is no unique inverse mapping (ill-posed problem) from the measurements onto the consumption of oxyhemoglobin (OHb) and deoxyhemoglobin (HHb) molecules in different parts of the cortex. One way to solve this inverse problem is to introduce mathematical constraints into the reconstruction algorithm. Furthermore, fNIRS source reconstruction is typically performed offline using standard inverse solvers not optimized for this type of data.

Another low-cost and mobile brain imaging modality is electroencephalogram (EEG). Compared with fNIRS, EEG devices have a better temporal resolution because they use scalp sensors (e.g., electrodes) to measure the macroscopic electrical activity generated by clusters of cortical neurons that synchronize in space and time. Like fNIRS, the inverse mapping from EEG voltage sensors onto cortical current dipoles is not unique, therefore, to solve this inverse problem constraints are also needed. As such, fNIRS and EEG data fusion is attractive for brain imaging because each modality can complement each other by bringing data-driven constraints into an inverse mapping algorithm in which each constraint is enforced at the right spatiotemporal scales.

Accordingly, multimodal wearable measurement systems that include both optical and electrical activity measurement components are described herein. An exemplary multimodal measurement system includes a wearable assembly configured to be worn by a user and comprising a plurality of light sources each configured to emit light directed at a target within the user, a plurality of detectors configured to detect arrival times for photons of the light after the light is scattered by the target, and a plurality of electrodes configured to be external to the user and detect electrical activity of the target. In some examples, the multimodal measurement system further includes a processing unit configured to generate optical measurement data based on the arrival times detected by the detectors and electrical measurement data based on the electrical activity detected by the electrodes. The processing unit may be further configured to process the optical measurement data and the electrical measurement data (e.g., in real time during operation of the detectors and electrodes) in accordance with a data fusion heuristic to generate an estimate of cortical source activity and/or otherwise determine one or more other physiological characteristics of a user.

The systems and methods described herein may provide various benefits. For example, the systems and methods described herein may be optimized for brain tomography based on a computationally efficient fusion of optical measurement data (e.g., fNIRS data) and electrical measurement data (e.g., EEG data). This fusion method may benefit brain mapping algorithms by providing data-driven spatiotemporal constraints at different temporal scales. In particular, the systems and methods described herein may allow for computationally efficient real-time imaging. This technology has the potential to improve basic neuro-scientific research as well as the development of imaging-based translational neurotechnologies, such as brain-computer interfaces (BCIs) and continuous brain monitoring.

These and other advantages and benefits of the present systems and methods are described more fully herein and/or will be made apparent in the description herein.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diode (sLEDs), vertical-cavity surface-emitting lasers (VCSELs), titanium sapphire lasers, a micro light emitting diodes (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
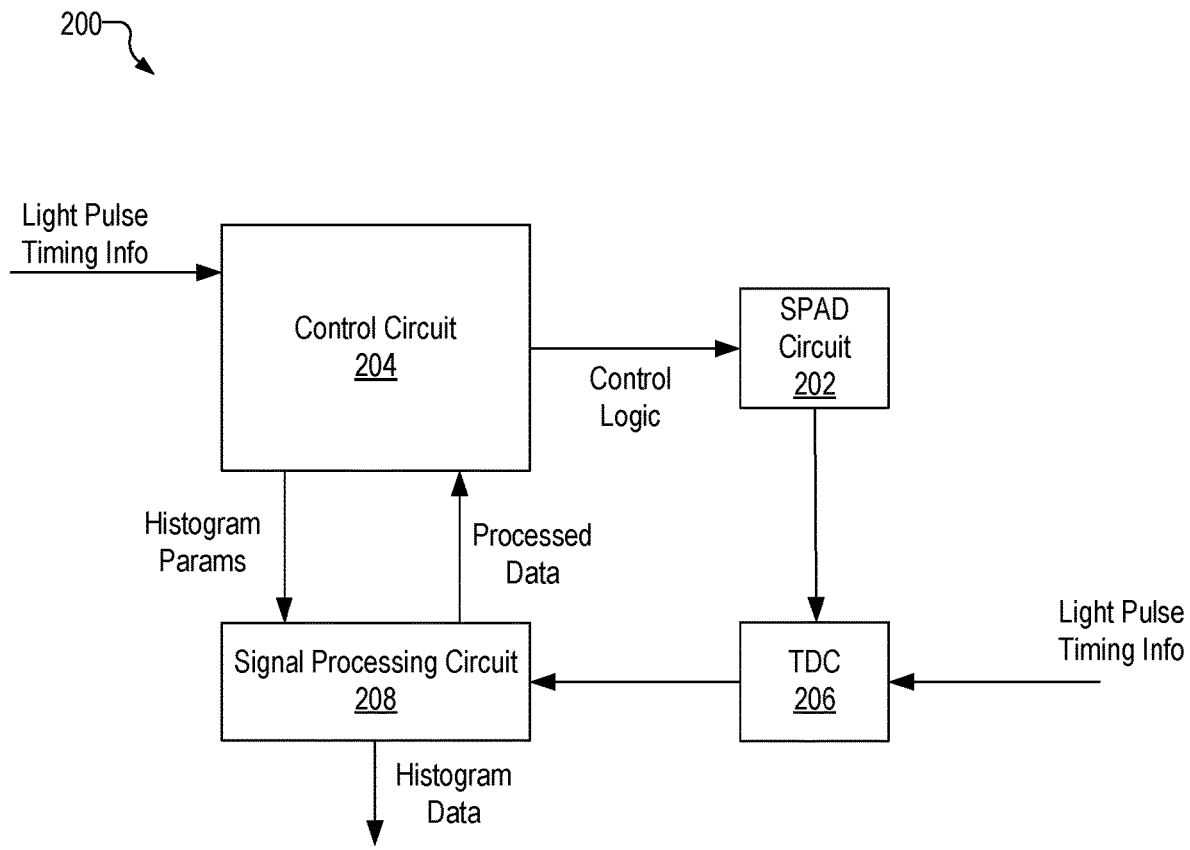
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters.

In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
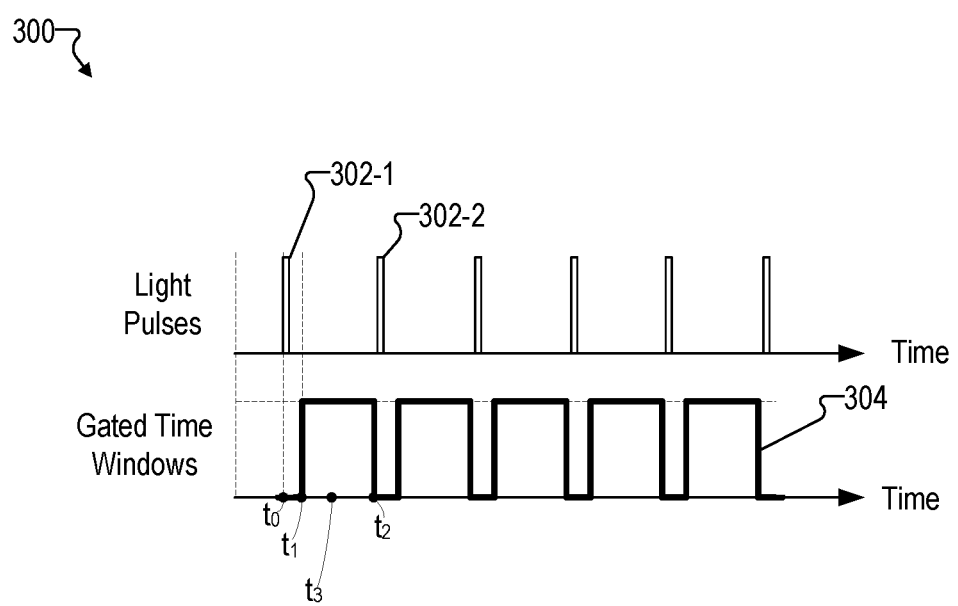
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
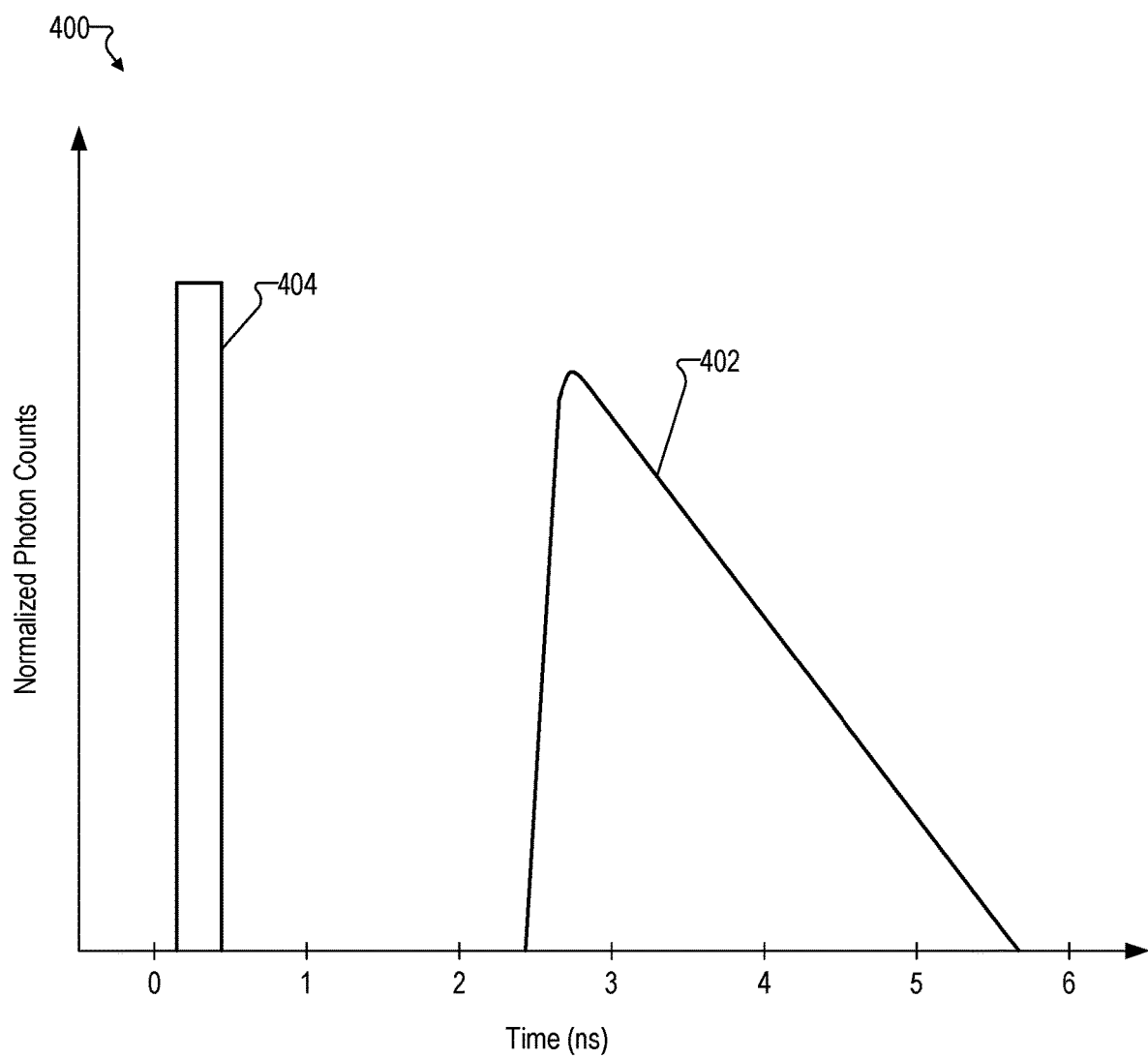
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a sub-assembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
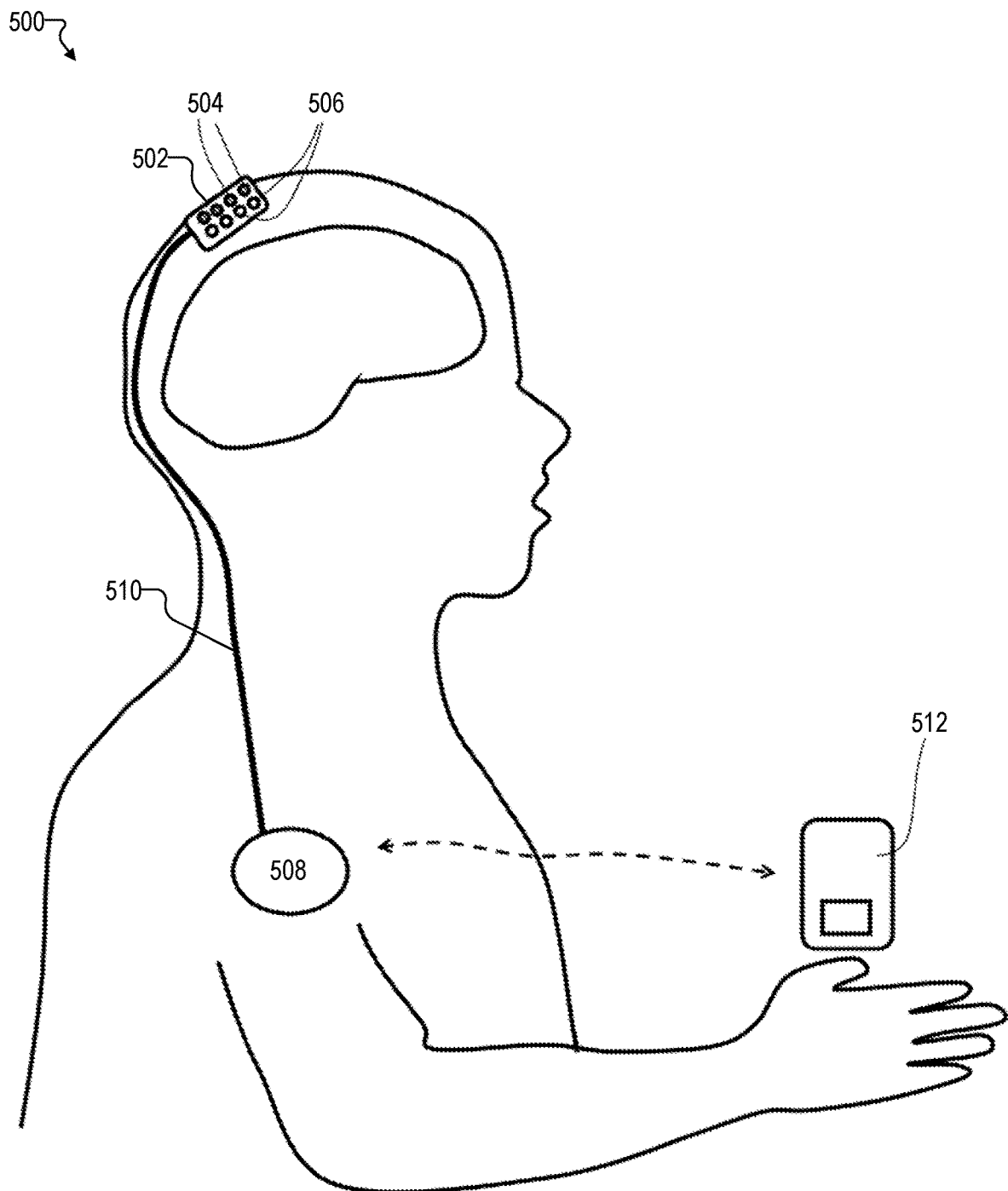
FIG. 5 illustrates an exemplary non-invasive wearable brain interface system.

To illustrate, FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Figure 6:
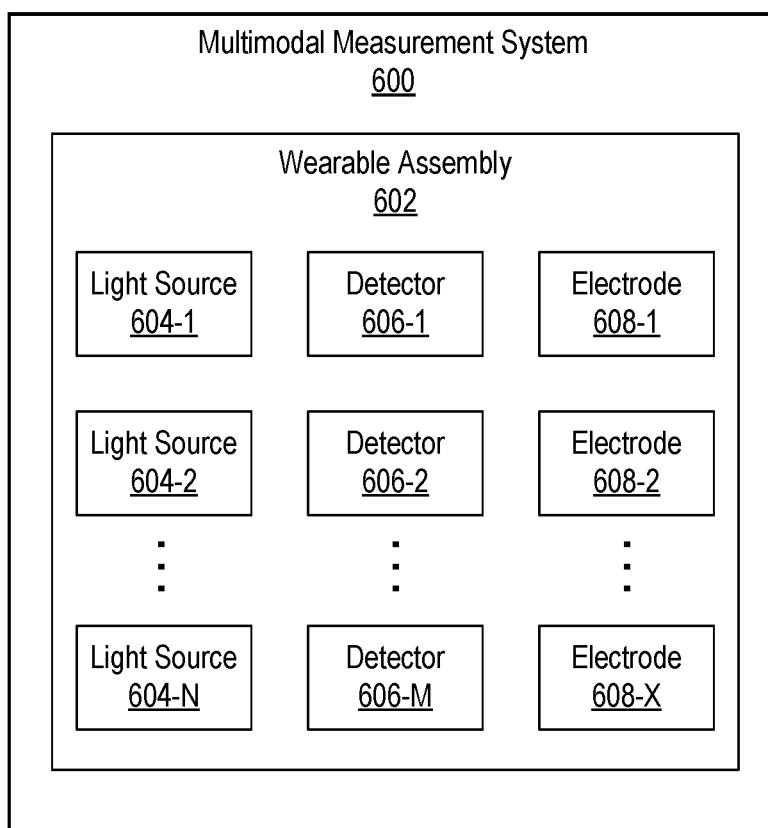
FIG. 6 shows an exemplary multimodal measurement system.

FIG. 6 shows an exemplary multimodal measurement system 600 in accordance with the principles described herein. Multimodal measurement system 600 may at least partially implement optical measurement system 100 and, as shown, includes a wearable assembly 602, which includes N light sources 604 (e.g., light sources 604-1 through 604-N), M detectors 606 (e.g., detectors 606-1 through 606-M), and X electrodes (e.g., electrodes 608-1 through 608-X). Multimodal measurement system 600 may include any of the other components of optical measurement system 100 as may serve a particular implementation. N, M, and X may each be any suitable value (i.e., there may be any number of light sources 604, any number of detectors 606, and any number of electrodes 608 included in multimodal measurement system 600 as may serve a particular implementation).

Light sources 604 are each configured to emit light (e.g., a sequence of light pulses) and may be implemented by any of the light sources described herein.

Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 606 may be implemented by any of the detectors described herein.

Electrodes 608 may be configured to detect electrical activity within a target (e.g., the brain). Such electrical activity may include EEG activity and/or any other suitable type of electrical activity as may serve a particular implementation. In some examples, electrodes 608 are all conductively coupled to one another to create a single channel that may be used to detect electrical activity. Alternatively, at least one electrode included in electrodes 608 is conductively isolated from a remaining number of electrodes included in electrodes 608 to create at least two channels that may be used to detect electrical activity.

Wearable assembly 602 may be implemented by any of the wearable devices, modular assemblies, and/or wearable units described herein. For example, wearable assembly 602 may be implemented by a wearable device (e.g., headgear) configured to be worn on a user's head. Wearable assembly 602 may additionally or alternatively be configured to be worn on any other part of a user's body.

Multimodal measurement system 600 may be modular in that one or more components of multimodal measurement system 600 may be removed, changed out, or otherwise modified as may serve a particular implementation. Additionally or alternatively, multimodal measurement system 600 may be modular such that one or more components of multimodal measurement system 600 may be housed in a separate housing (e.g., module) and/or may be movable relative to other components. Exemplary modular multimodal measurement systems are described in more detail in U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038,481, filed Jun. 12, 2020, and U.S. Provisional Patent Application No. 63/064,688, filed Aug. 12, 2020, which applications are incorporated herein by reference in their respective entireties.

To illustrate, various modular assemblies that may implement multimodal measurement system 600 are described in connection with FIGS. 7-9. The modular assemblies described herein are merely illustrative of the many different implementations of multimodal measurement system 600 that may be realized in accordance with the principles described herein. Each of the modular assemblies described herein may include one or more modules and may be worn on the head or any other suitable body part of the user.

Figure 7:
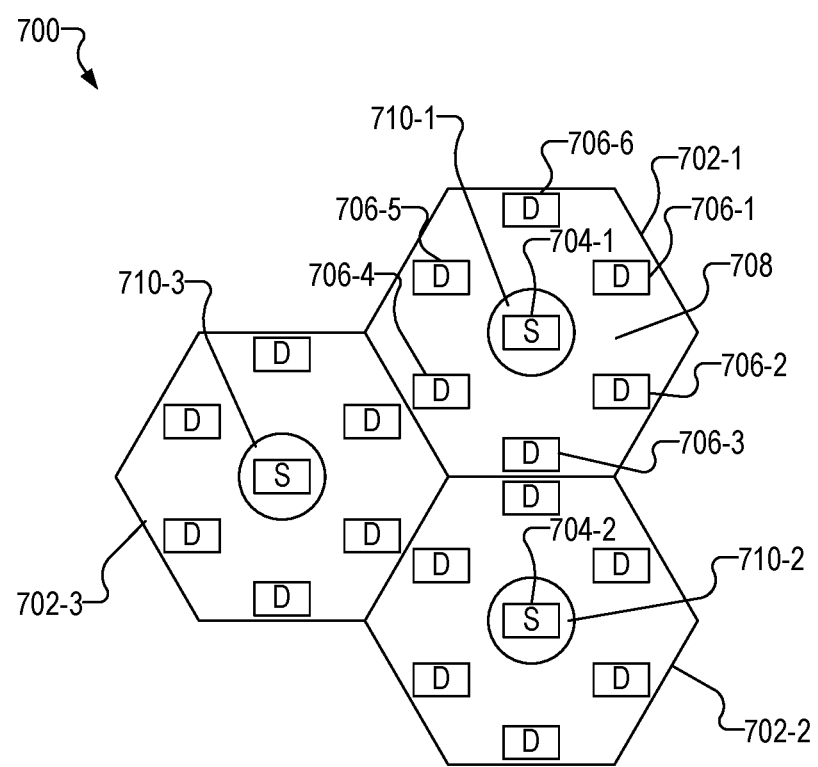
FIGS. 7-9 illustrates various modular assemblies.
Figure 8A:
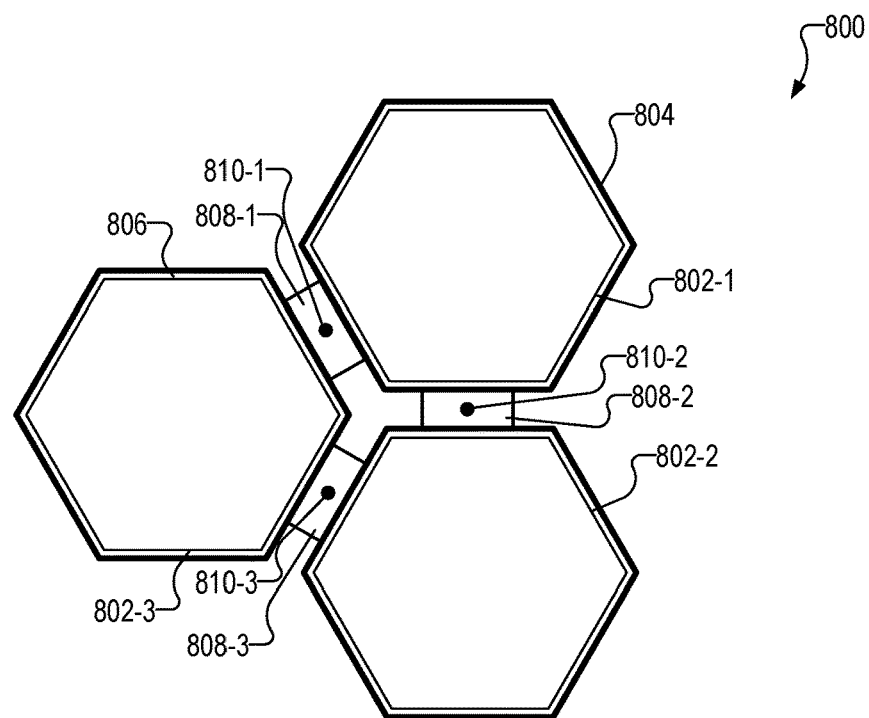
Figure 8B:
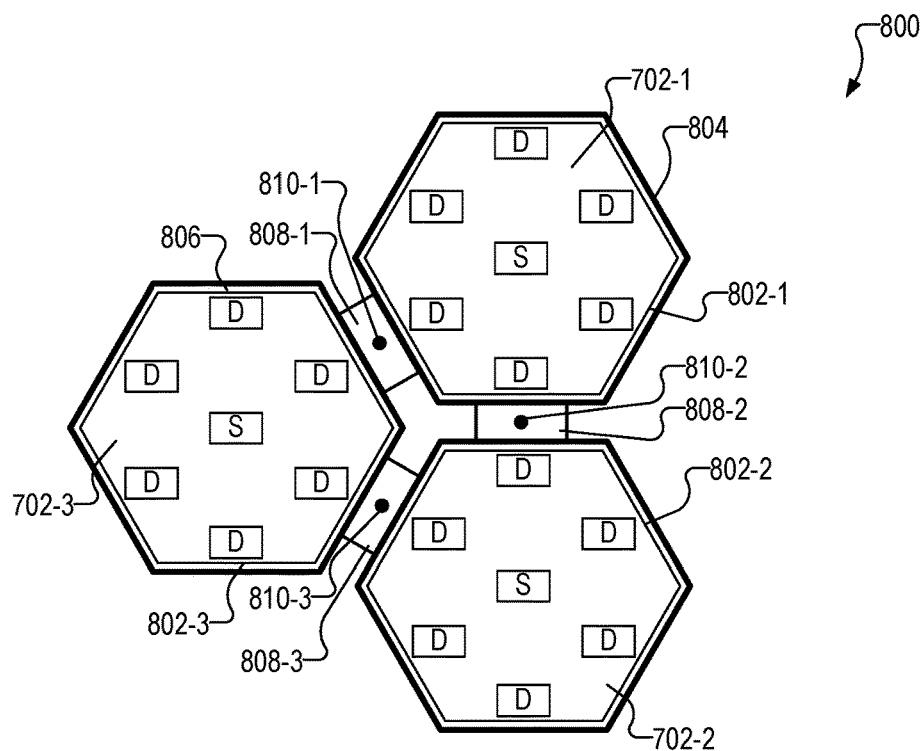
Figure 9:
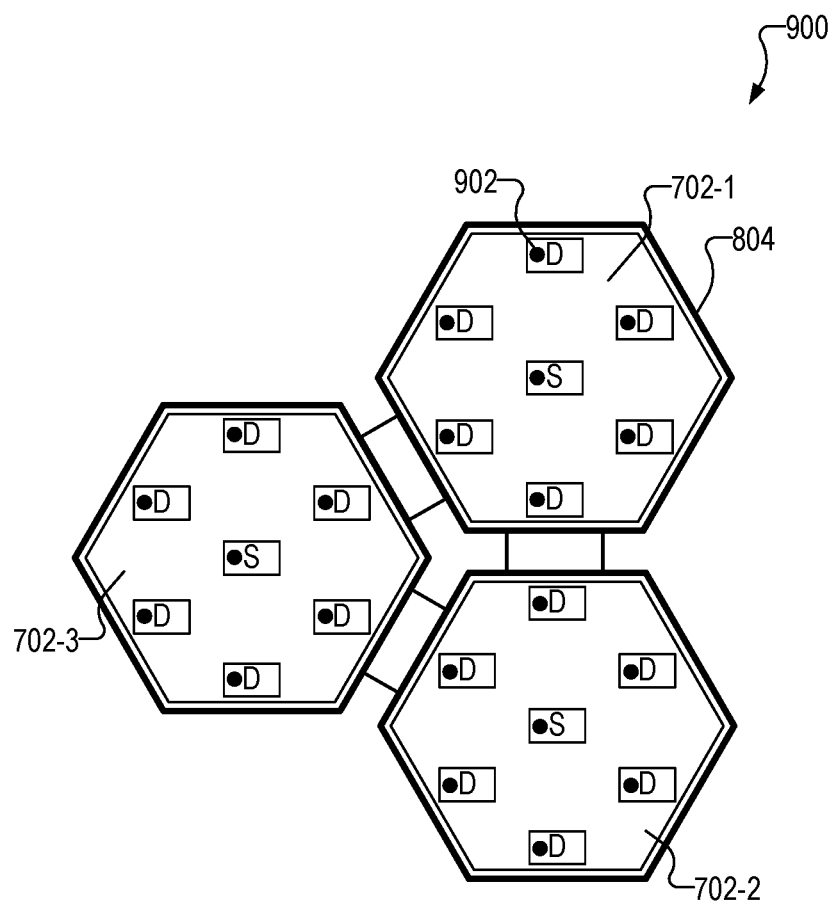

In FIGS. 7-9, the illustrated modules may, in some examples, be physically distinct from each other. For example, as described herein, each module may be configured to be removably attached to a wearable assembly (e.g., by being inserted into a different slot of the wearable assembly). This may allow the modular assemblies to conform to three-dimensional surface geometries, such as a user's head.

In FIGS. 7-9, each illustrated module may include one or more light sources labeled "S" and a set of detectors each labeled "D". Some specific light sources and detectors are also referred to by specific reference numbers.

Each light source depicted in FIGS. 7-9 may be implemented by one or more light sources similar to light source 110 and may be configured to emit light directed at a target (e.g., the brain).

In some examples, each light source may be implemented by dual (e.g., two) light sources that are co-located (e.g., right next to each other within the same module). For example, a module may include a first light source and a second light source. In this configuration, the first light source may emit light having a first wavelength and the second light source may emit light having a second wavelength different than the first wavelength. This dual light source configuration may be used when it is desired for the multimodal measurement system to concurrently measure or detect different properties. For example, pairs of lights sources operating at different wavelengths may be used to measure the concentrations of oxygenated and deoxygenated hemoglobin, which are at different wavelengths.

Each detector depicted in FIGS. 7-9 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

FIG. 7 shows an illustrative modular assembly 700 that may implement multimodal measurement system 600. As shown, modular assembly 700 includes a plurality of modules 702 (e.g., modules 702-1 through 702-3). While three modules 702 are shown to be included in modular assembly 700, in alternative configurations, any number of modules 702 (e.g., a single module up to sixteen or more modules) may be included in modular assembly 700. Moreover, while each module 702 has a hexagonal shape, modules 702 may alternatively have any other suitable geometry (e.g., in the shape of a pentagon, octagon, square, rectangular, circular, triangular, free-form, etc.).

Each module 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module 702 includes a single light source and six detectors. Alternatively, each module 702 may have any other number of light sources (e.g., two light sources) and any other number of detectors.

Each light source (e.g., light source 704-1 or light source 704-2) depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

The detectors of a module may be distributed around the light source of the module. For example, detectors 706 of module 702-1 are distributed around light source 704-1 on surface 708 of module 702-1. In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling, etc.) information about the detected signals. Detectors of a module may be alternatively disposed on the module as may serve a particular implementation.

As shown, modular assembly 700 further includes a plurality of electrodes 710 (e.g., electrodes 710-1 through 710-3), which may implement electrodes 608. Electrodes 710 may be located at any suitable location that allows electrodes 710 to be in physical contact with a surface (e.g., the scalp and/or skin) of a body of a user. For example, in modular assembly 700, each electrode 710 is on a module surface configured to face a surface of a user's body when modular assembly 700 is worn by the user. To illustrate, electrode 710-1 is on surface 708 of module 702-1. Moreover, in modular assembly 700, electrodes 710 are located in a center region of each module 702 and surround each module's light source 704. Alternative locations and configurations for electrodes 710 are described herein.

In FIG. 7, modules 702 are shown to be adjacent to and touching one another. Modules 702 may alternatively be spaced apart from one another. For example, FIGS. 8A-8B show another modular assembly 800 that may implement multimodal measurement system 600. In modular assembly 800, modules 702 may be configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

As shown in FIGS. 8A-8B, wearable assembly 804 may include a plurality of connecting structures 808 (e.g., connecting structures 808-1 through 808-3) configured to interconnect each slot 802 of wearable assembly 804. Connecting structures 808 may be implemented by any suitable connecting mechanisms (e.g., ball joints, hinges, elastic bands, etc.) and/or support members (e.g., support frames, bands, rails, etc.). In some examples, connecting structures 808 are flexible and/or movable such that modular assembly 800 may be adjusted to fit a particular body part (e.g., the head). Moreover, with such a configuration, modular assembly 800 can be adjusted to conform to a 3D (non-planar) surface, such as a user's head, and/or to target a specific region of interest (e.g., a specific region of the brain).

As shown in FIGS. 8A-8B, electrodes 810 (e.g., electrodes 810-1 through 810-3) that implement electrodes 608 may be located off-module (i.e., not on any of modules 702) on connecting structures 808. Additionally or alternatively, one or more electrodes may be located off-module on any other structure or component of wearable assembly 804 as may serve a particular implementation.

FIG. 9 shows another modular assembly 900 that may implement multimodal measurement system 600. Modular assembly 900 is similar to modular assembly 800, except that in modular assembly 900, electrodes (e.g., electrode 902) that implement electrodes 608 are on (e.g., integrated into) each of the light sources and detectors of modules 702. The electrodes may be integrated into one or more of sources and detectors of modules 702 in any suitable manner. For example, the light sources and detectors may be implemented by light guides that have distal ends configured to be in contact with a surface of a body of the user. In this example, the electrodes may be integrated into the light guides themselves.

Figure 10:
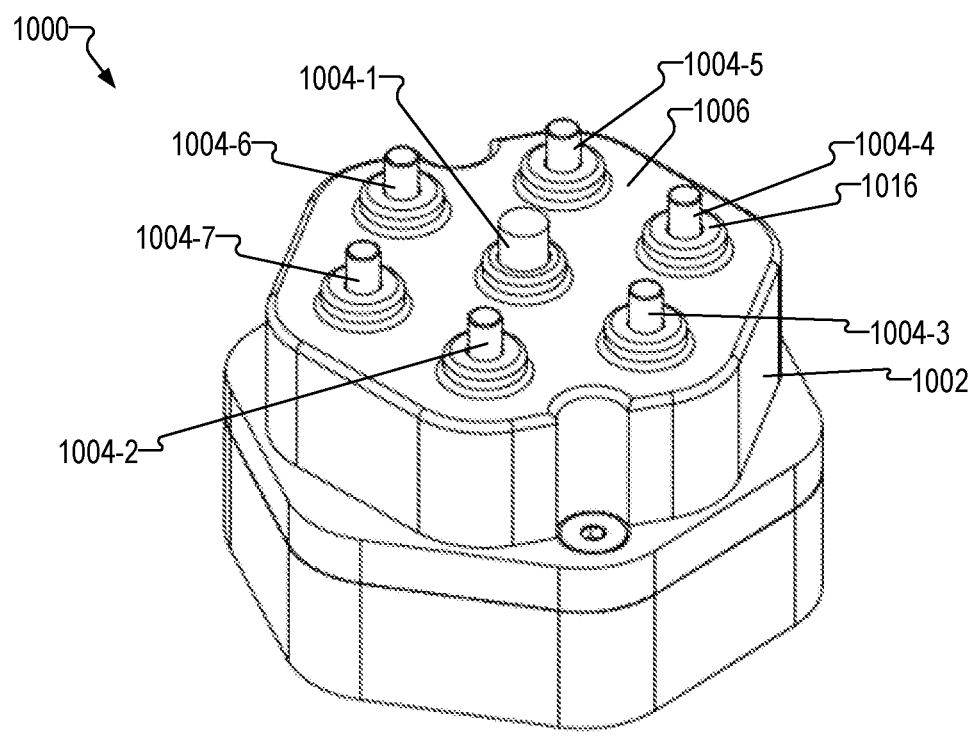
FIG. 10 shows a perspective view of a module.

To illustrate, FIG. 10 shows a perspective view of a module 1000 that may implement any of the modules described herein. Module 1000 is described in more detail in U.S. Provisional Patent Application No. 63/064,688, filed Aug. 12, 2020, the contents of which are incorporated herein by reference in their entirety.

As shown in FIG. 10, module 1000 includes a housing 1002 and a plurality of light guides 1004 (e.g., light guides 1004-1 through 1004-7) protruding from an upper surface 1006 of housing 1002. As used herein with reference to module 1000, "upper" refers to a side of module 1000 that faces a target within a body of a user when module 1000 is worn by the user.

In FIG. 10, light guide 1004-1 is part of a light source assembly included in module 1000. As such, light may pass through light guide 1004-1 towards the target while module 1000 is being worn by the user. Light guides 1004-2 through 1004-7 are parts of detector assemblies included in module 1000. As such, light may be received by light guides 1004-2 through 1004-7 after the light is scattered by the target.

In some examples, a least a portion of light guides 1004 are made out of a conductive material, which allows light guides 1004 themselves to function as the electrodes that implement electrodes 608.

Figure 11:
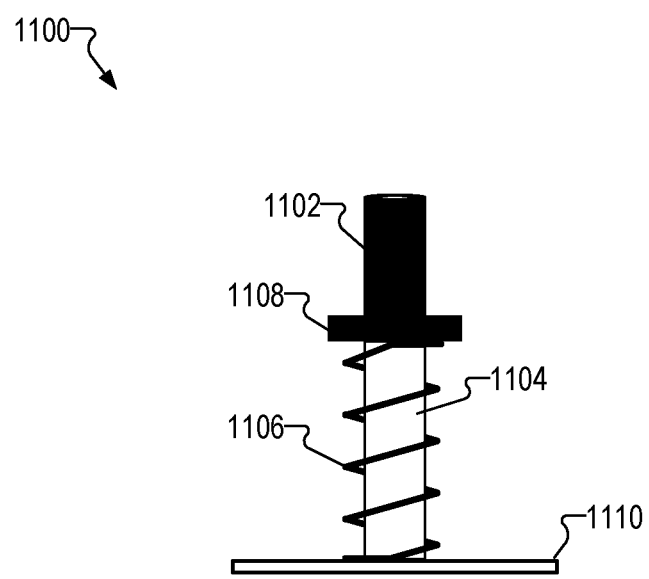
FIG. 11 shows an exemplary light guide assembly.

To illustrate, FIG. 11 shows an exemplary light guide assembly 1100 that may implement any of the light guides 1004 shown in FIG. 10. As shown, light guide assembly 1100 includes an upper light guide portion 1102, a lower light guide portion 1104, a spring member 1106, and a flange 1108 in between upper and lower light guide portions 1102 and 1104. FIG. 11 also depicts a printed circuit board (PCB) 1110 attached to a proximal end of lower light guide portion 1104.

In some examples, lower light guide portion 1104, spring member 1106, flange 1108, and PCB 1110 are configured to be housed within housing 1002 of module 1000, while upper light guide portion 1102 is configured to protrude from upper surface 1006 of housing 1002. In this configuration, upper light guide portion 1102 may be in contact with a surface of a user.

In the example of FIG. 11, upper light guide portion 1102 and flange 1008 are made out of a conductive material, which allows a distal end of the upper light guide portion 1102 to function as an electrode that may be used to detect electrical activity within the a target. This conductive portion may be conductively coupled to spring member 1106, which is also conductive. In this manner, spring member 1106 may conductively couple the conductive portion of upper light guide portion 1102 with circuitry included on PCB 1110. The circuitry may be configured to process the electrical activity detected by the electrode implemented by the conductive upper light guide portion 1102 in any of the ways described herein.

In some alternative example, both upper and lower light guide portions 1102 and 1104 are made out of the conductive material.

As shown, spring member 1106 comprises a coil spring positioned around an external surface of lower light guide portion 1104. A proximal end of spring member 1106 pushes against PCB 1110 (or any other suitable support structure), while the distal end of spring member 1106 pushes against flange 1108. Flange 1108 may be any suitable structure (e.g., a ring) attached to or protruding from upper light guide portion 1102 and/or lower light guide portion 1104. By pressing against flange 1108, spring member 1106 pushes the distal end of upper light guide portion 1102 away from upper surface 1006 of housing 1002 (shown in FIG. 10). In this manner, the distal end of upper light guide portion 1102 may be biased away from upper surface 1006 of housing 1002 and toward the user's body.

Figure 12A:
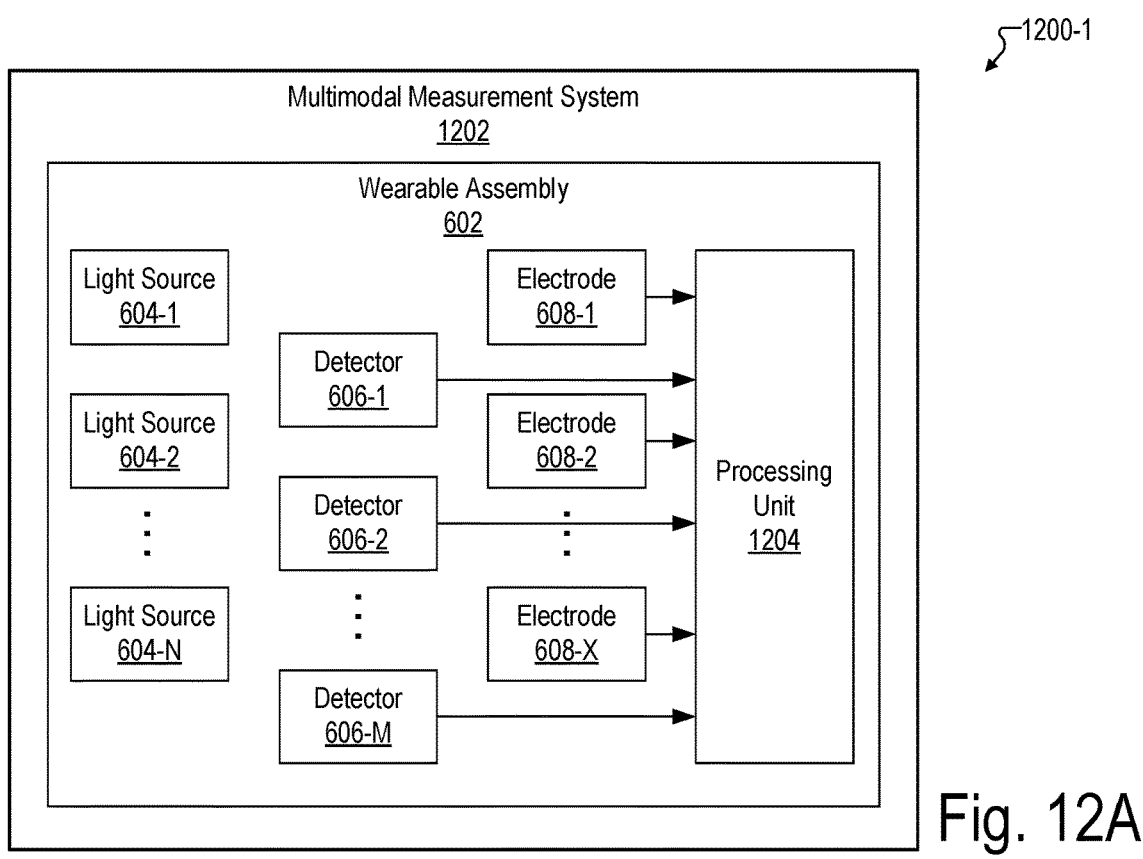
FIGS. 12A-12B show illustrative configurations of an exemplary multimodal measurement system.
Figure 12B:
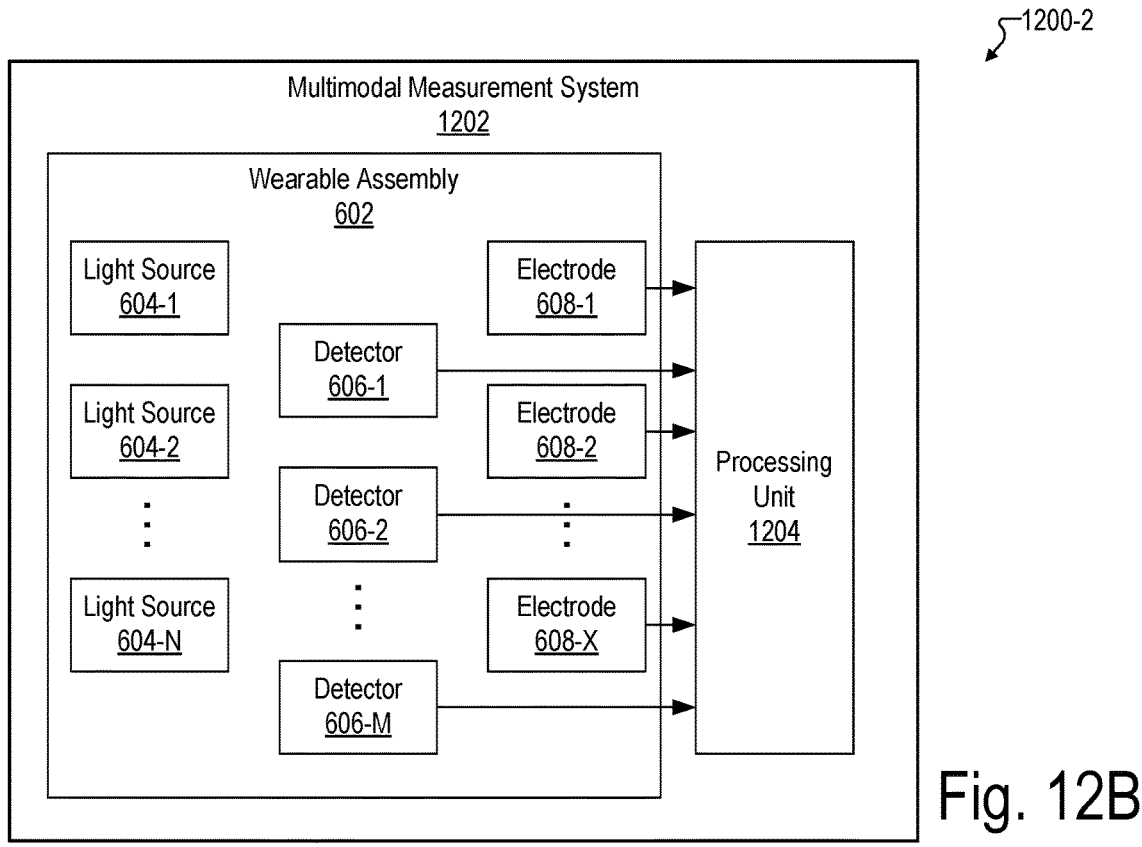

In some examples, the multimodal measurement systems described herein may further include a processing unit configured to perform one or more operations based on photon arrival times detected by the detectors described herein and the electrical activity detected by the electrodes described herein. For example, FIGS. 12A-12B show illustrative configurations 1200-1 and 1200-2 of an exemplary multimodal measurement system 1202 in accordance with the principles described herein.

Multimodal measurement system 1202 may be an implementation of multimodal measurement system 600 and, as shown, includes the wearable assembly 602, light sources 604, detectors 606, and electrodes 608 described in connection with FIG. 6.

In configuration 1200-1, a processing unit 1204 is also included in wearable assembly 602. In configuration 1200-2, processing unit 1204 is not included in wearable assembly 602 (i.e., processing unit 1204 is located external to wearable assembly 602). Either configuration 1200-1 or 1200-2 may be used in accordance with the systems, circuits, and methods described herein.

In configuration 1200-2, processing unit 1204 is not included in wearable assembly 602. For example, processing unit 1204 may be included in a wearable device separate from wearable assembly 602. To illustrate, processing unit 1204 may be included in a wearable device configured to be worn off the head (e.g., on a belt) while wearable assembly 602 is worn on the head. In these examples, one or more communication interfaces (e.g., cables, wireless interfaces, etc.) may be used to facilitate communication between wearable assembly 602 and the separate wearable device.

Additionally or alternatively, in configuration 1200-2, processing unit 1204 may be remote from the user (i.e., not worn by the user). For example, processing unit 1204 may be implemented by a stand-alone computing device communicatively coupled to wearable assembly 602 by way of one or more communication interfaces (e.g., cables, wireless interfaces, etc.).

In some examples, processing unit 1204 may be distributed between multiple devices and/or multiple locations as may serve a particular implementation. Processing unit 1204 may be implemented by processor 108, controller 112, control circuit 204, and/or any other suitable processing and/or computing device or circuit.

Figure 13:
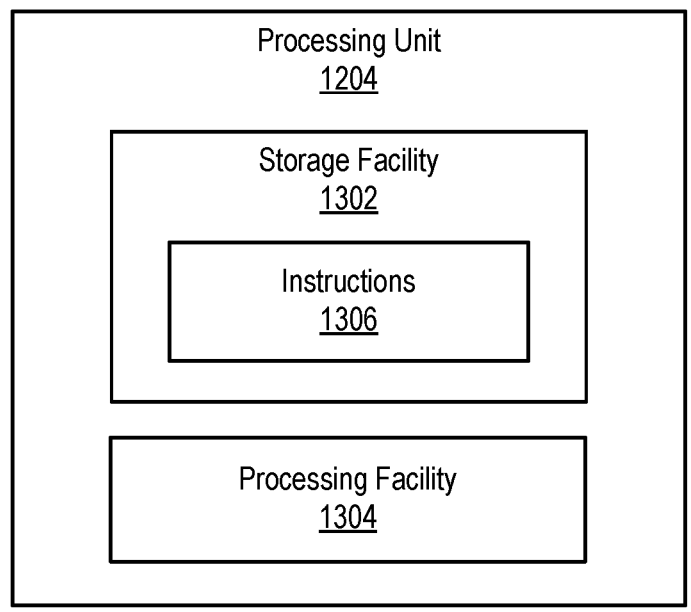
FIG. 13 illustrates an exemplary processing unit.

For example, FIG. 13 illustrates an exemplary implementation of processing unit 1204 in which processing unit 1204 includes a memory (storage facility) 1302 and a processor (processing facility) 1304 configured to be selectively and communicatively coupled to one another. In some examples, memory 1302 and processor 1304 may be distributed between multiple devices and/or multiple locations as may serve a particular implementation.

Memory 1302 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1302 may maintain (e.g., store) executable data used by processor 1304 to perform one or more of the operations described herein. For example, memory 1302 may store instructions 1306 that may be executed by processor 1304 to perform any of the operations described herein. Instructions 1306 may be implemented by any suitable application, program (e.g., sound processing program), software, code, and/or other executable data instance. Memory 1302 may also maintain any data received, generated, managed, used, and/or transmitted by processor 1304.

Processor 1304 may be configured to perform (e.g., execute instructions 1306 stored in memory 1302 to perform) various operations described herein. For example, processor 1304 may be configured to perform any of the operations described herein as being performed by processing unit 1204.

Processing unit 1204 may be configured to generate optical measurement data (e.g., fNIRS data) based on the arrival times detected by detectors 606 and electrical measurement data (e.g., EEG data) based on the electrical activity detected by electrodes 608. This may be performed in any suitable manner.

For example, processing unit 1204 may be configured to process the optical measurement data and the electrical measurement data in accordance with a data fusion heuristic to generate an estimate of cortical source activity. In some examples, this may be performed in real-time while detectors 606 are detecting the arrival times and electrodes 608 are detecting the electrical activity.

To illustrate, an exemplary data fusion heuristic that may be employed by processing unit 1204 with respect to fNIRS and EEG data will now be described. The operations described herein assimilate samples of each modality as they become available and update the current estimates of cortical source activity in real time.

For the observation equation of the EEG, a standard linear propagation model may be represented by the following equation.

$$v_k = Ls_k + n_k \quad (1)$$

In equation 1, $v_k$ is a vector of voltages collected in the EEG sensors at instant k, L is the so-called lead field matrix that describes the propagation of electrical activity generated by sources in the cortex to the sensors, and $s_k$ is the amplitude of the current source density in different parts of the cortex at sample time k, and $n_k$ is a sensor noise vector. The lead field matrix can be precomputed based on a model of the head derived from magnetic resonance imaging (MRI) data or an established atlas. For the observation equation of fNIRS, the following linearized model may be used.

$$f_k = Ja_k + m_k \quad (2)$$

In equation 2, $f_k$ is a sample of oxy and deoxy absorption, J=MS, factorizes into the product of the MBLL linear transformation and sensitivity matrix S, $a_k$ is a vector of light absorption on each location of the source space, and $m_k$ is optical sensor noise. The matrices M and S can be precomputed. To link the light absorption signal $a_k$ with the cortical electrical activity $s_k$ in a computationally tractable manner, the following convolution model may be used.

$$a_k = \sum_{i=0}^{n} h_i s_{k-i} \quad (3)$$

In equation 3, the $h_i$ coefficients represent a low-pass FIR filter. Utilizing this approach allows for a fusion of EEG and fNIRS data that provides a method to link delay and strength of activation between the two modalities.

The data fusion heuristic described herein addresses at least two problems: 1) estimation of the vector time series of source activation $s_k$ from the time series of sensor data $v_k$ and $f_k$, and 2) estimation of the filter coefficients $h_i$ from the source time series $s_k$ and $a_k$.

To address the first problem, equation 3 is plugged into equation 2 yielding:

$$f_k = J\left(\sum_{i}^{n} h_i s_{k-i}\right) + m_k \quad (4)$$

$$f_k = Jh_1 s_k + \underbrace{\left(\sum_{i=1}^{n} h_i s_{k-i}\right)}_{S_{k-1}} + m_k$$

In equation 4, $S_{k-1}$ is the low-pass filtered version of the source time series up to the k−1 sample and can be considered fixed and known at the moment of estimating the $s_k$ source vector. Equation 4 may be used to rewrite equations 1 and 2 in a more compact way as follows:

$$\begin{bmatrix} v_k \\ f_k \end{bmatrix} = \begin{bmatrix} L \\ J \end{bmatrix} s_k + \begin{bmatrix} 0 \\ J \end{bmatrix} S_{k-1} + \begin{bmatrix} n_k \\ m_k \end{bmatrix} \quad (5)$$

Equation 5 is an ill-posed system because there are many more unknown sources than sensors. Hence, it may be solved for $s_k$ using a penalized least squares algorithm. To solve the second problem, equation 3 is rewritten in matrix form as follows.

$$A_k = Sh \quad (6)$$

In equation 6, $A_k = [a_k, \ldots, a_{k-N}]$ is a segment of light absorption signal and S is an embedding of past s source electrical activity. Equation 6 may be solved using least squares linear regression or any other suitable technique.

FIGS. 14-19 illustrate embodiments of a wearable device 1400 that includes elements of the multimodal detection systems described herein. In particular, the wearable devices 1400 shown in FIGS. 14-19 include a plurality of modules 1402, similar to any of the modules and module configurations described herein. For example, each module 1402 may include a light source, a plurality of detectors, and one or more electrodes. The wearable devices 1400 may each also include a controller (e.g., controller 112) and a processor (e.g., processor 108) and/or be communicatively connected to a controller and processor. In general, wearable device 1400 may be implemented by any suitable headgear and/or clothing article configured to be worn by a user. The headgear and/or clothing article may include batteries, cables, and/or other peripherals for the components of the multimodal measurement systems described herein.

Figure 14:
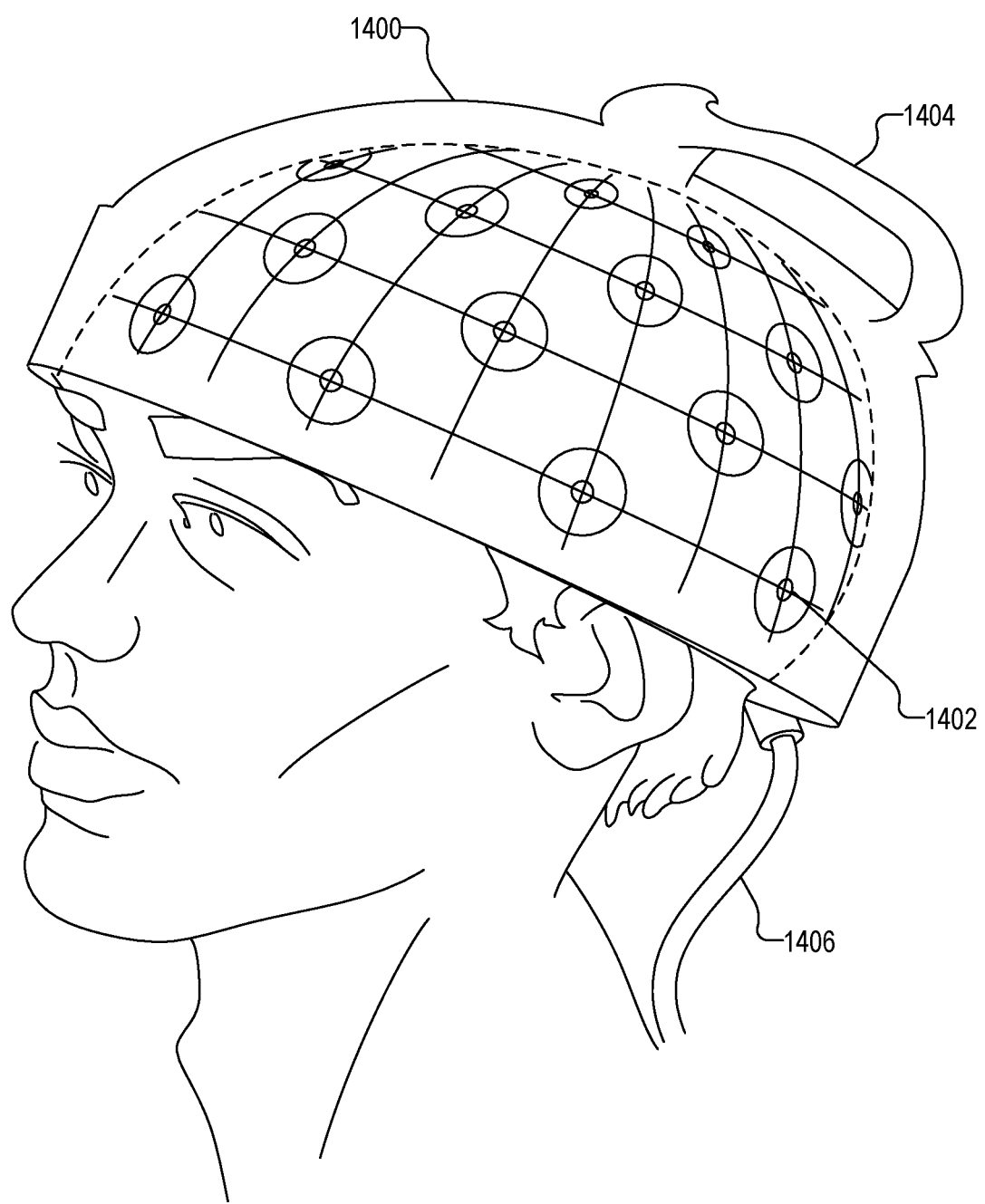
FIGS. 14-19 illustrate embodiments of a wearable device that includes elements of the optical detection systems described herein.
Figure 15:
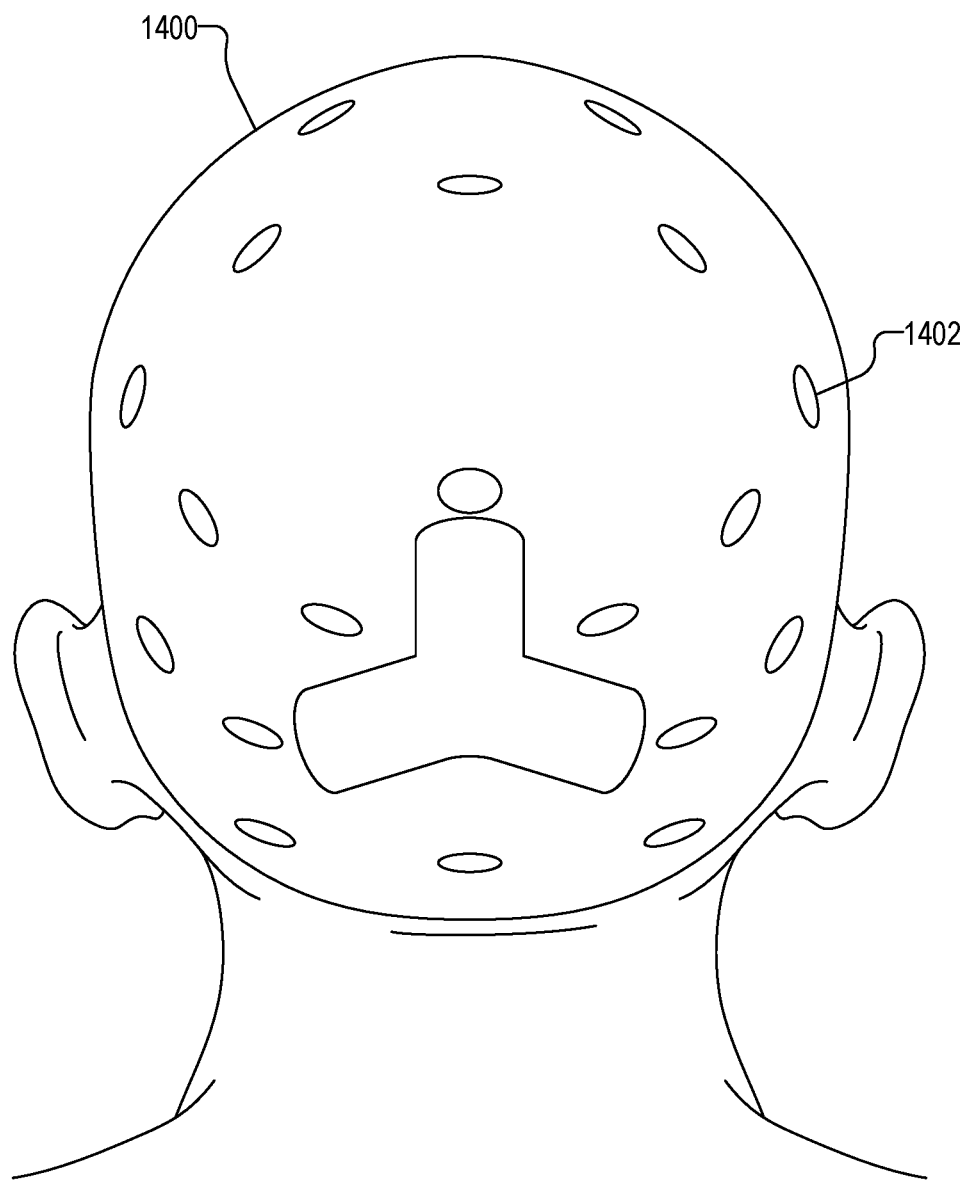
Figure 16:
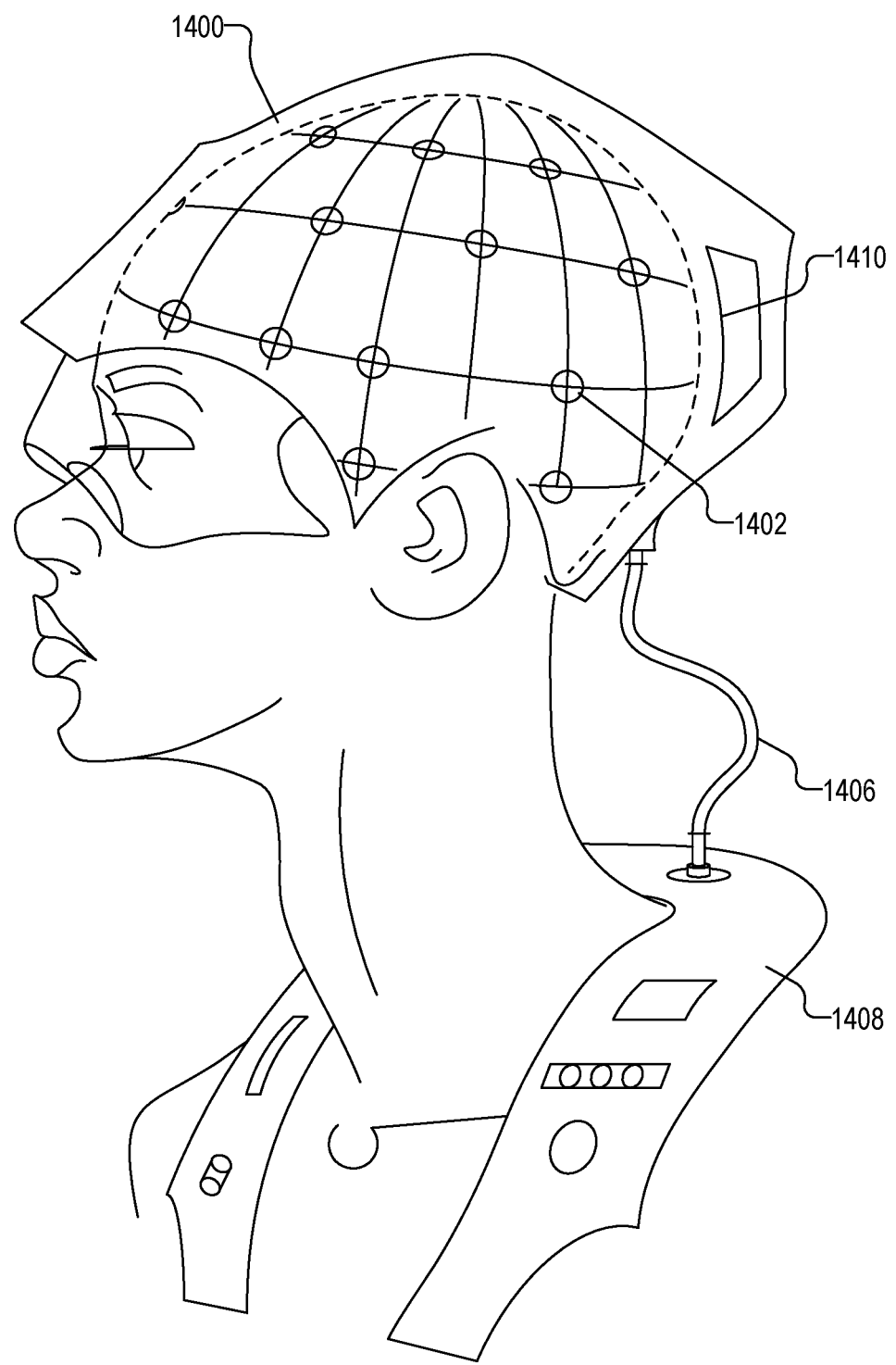

FIG. 14 illustrates an embodiment of a wearable device 1400 in the form of a helmet with a handle 1404. A cable 1406 extends from the wearable device 1400 for attachment to a battery or hub (with components such as a processor or the like). FIG. 15 illustrates another embodiment of a wearable device 1400 in the form of a helmet showing a back view. FIG. 16 illustrates a third embodiment of a wearable device 1400 in the form of a helmet with the cable 1406 leading to a wearable garment 1408 (such as a vest or partial vest) that can include a battery or a hub. Alternatively or additionally, the wearable device 1400 can include a crest 1410 or other protrusion for placement of the hub or battery.

Figure 17:
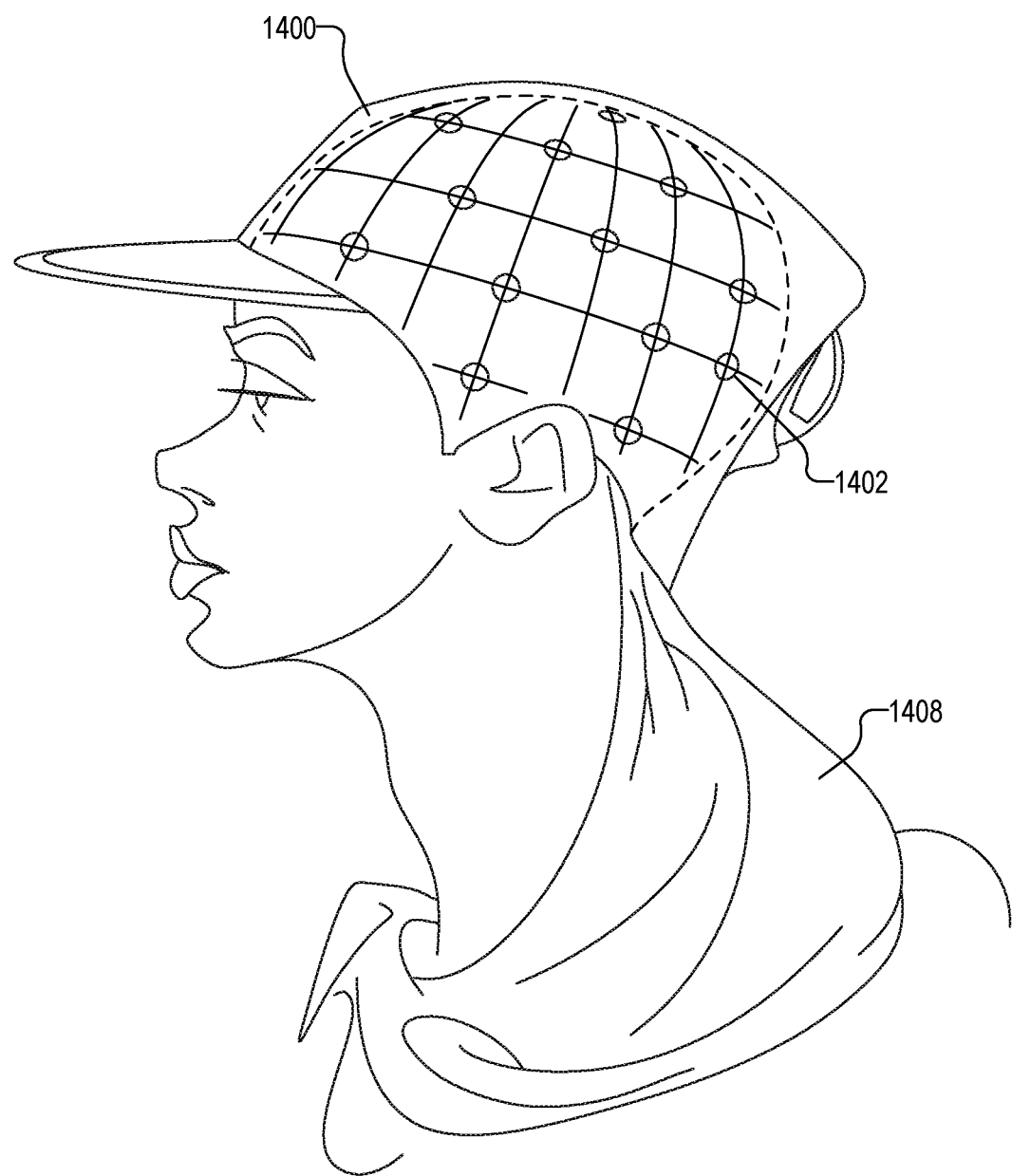
Figure 18:
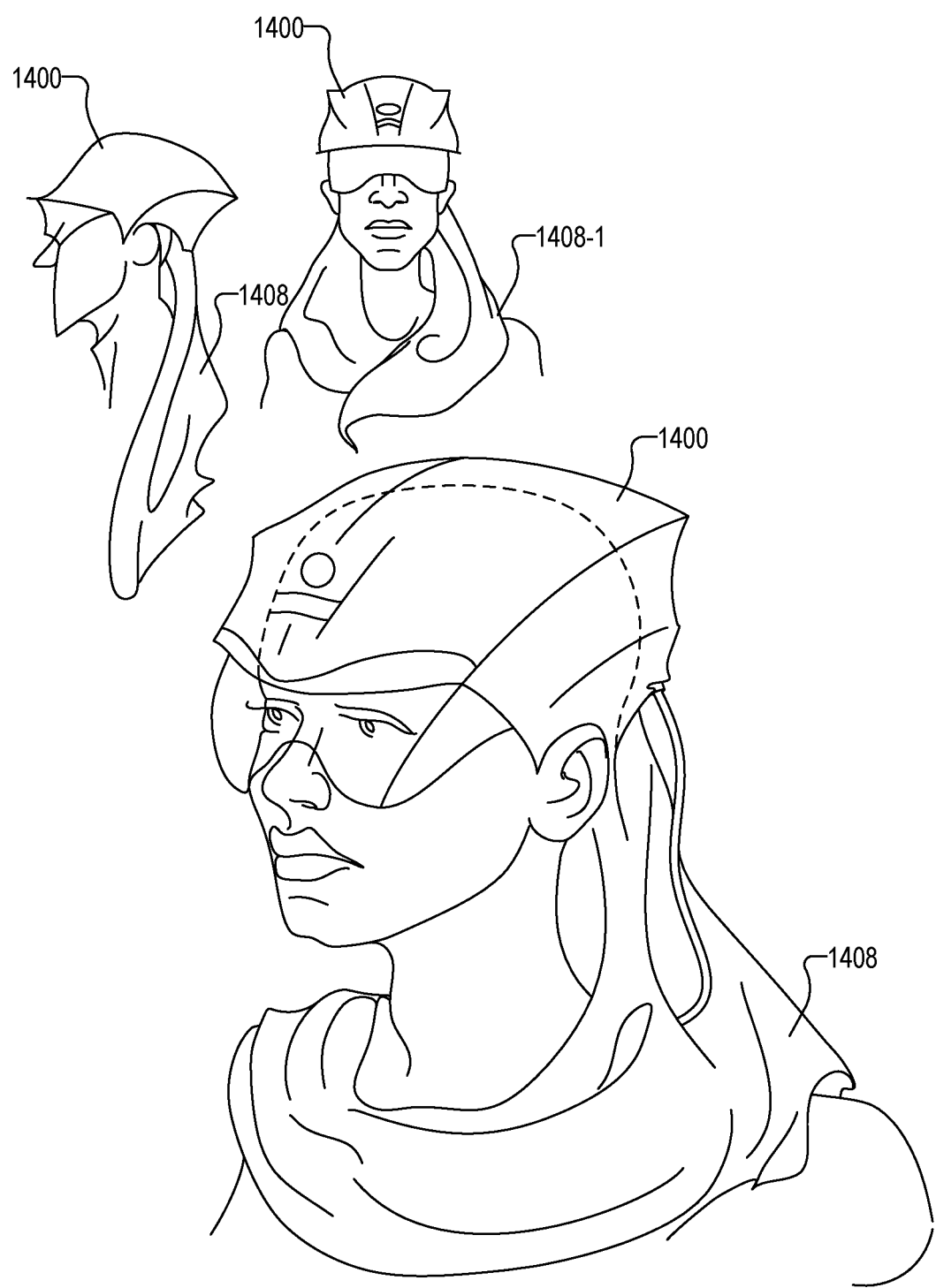
Figure 19:
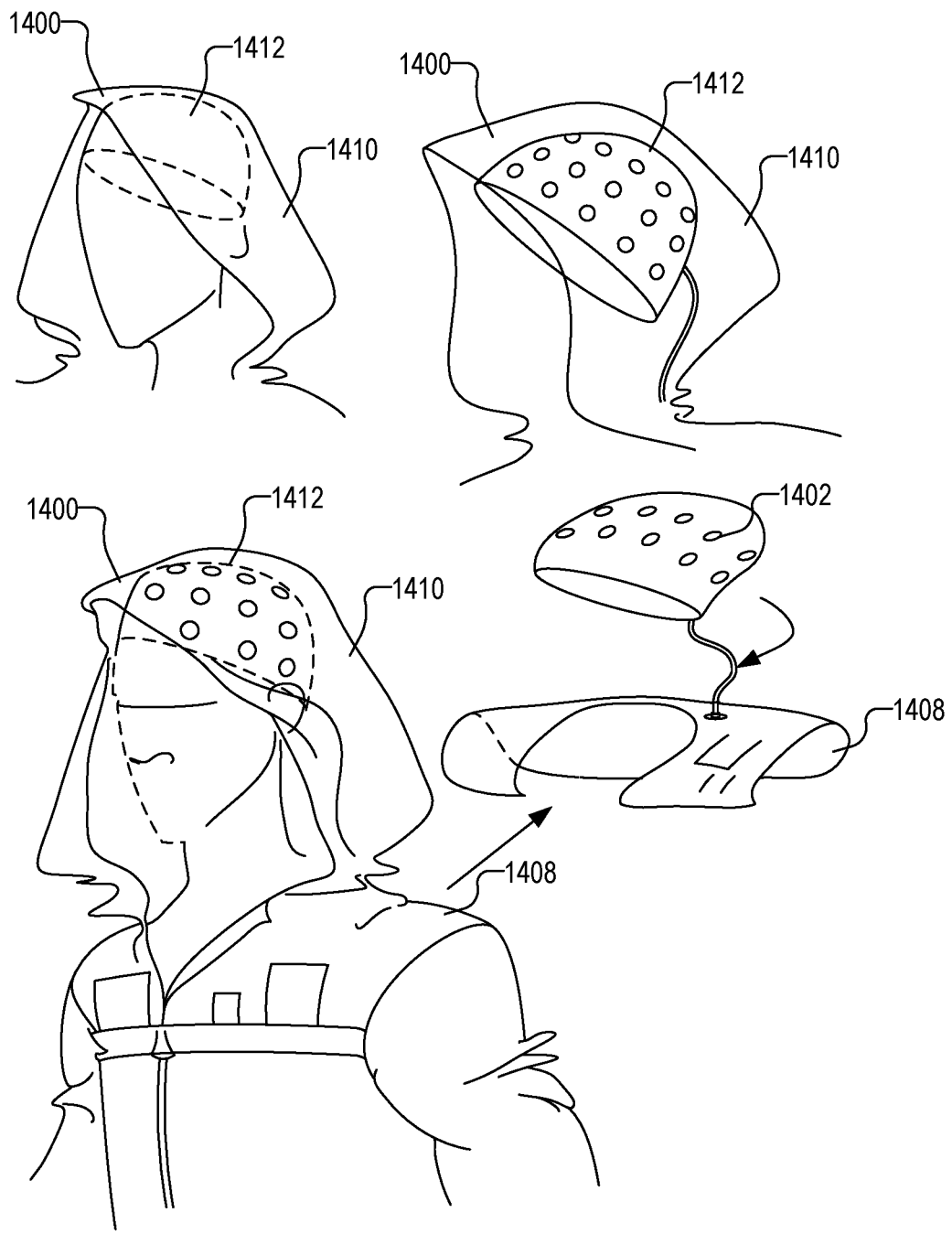

FIG. 17 illustrates another embodiment of a wearable device 1400 in the form of a cap with a wearable garment 1408 in the form of a scarf that may contain or conceal a cable, battery, and/or hub. FIG. 18 illustrates additional embodiments of a wearable device 1400 in the form of a helmet with a one-piece scarf 1408 or two-piece scarf 1408-1. FIG. 19 illustrates an embodiment of a wearable device 1400 that includes a hood 1410 and a beanie 1412 which contains the modules 1402, as well as a wearable garment 1408 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 20:
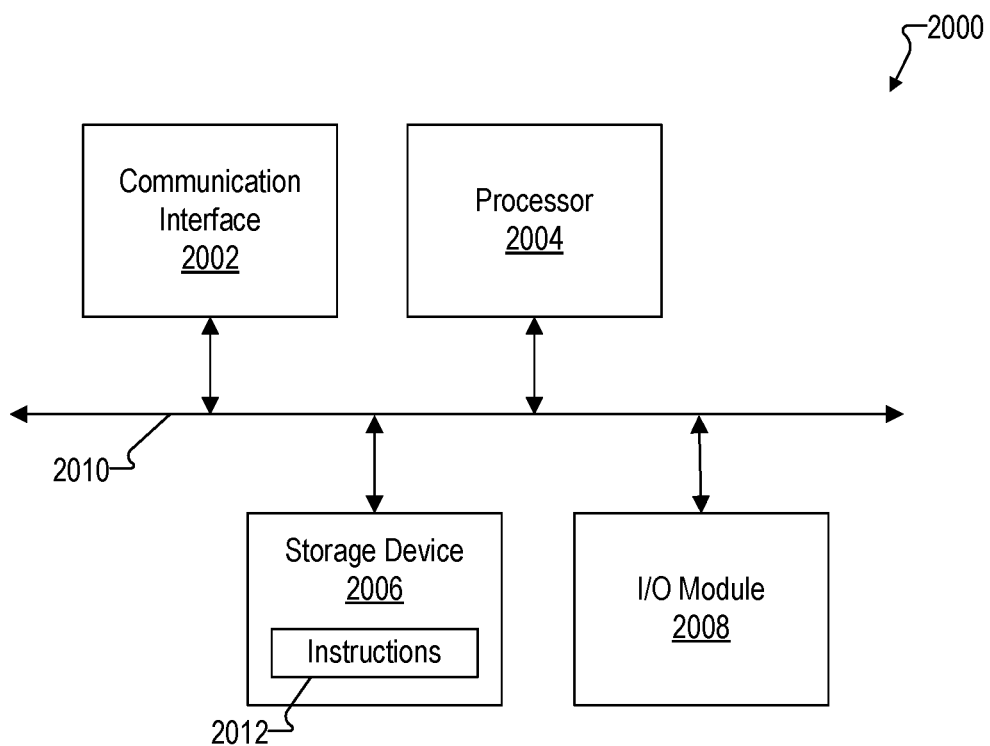
FIG. 20 illustrates an exemplary computing device.

FIG. 20 illustrates an exemplary computing device 2000 that may be specifically configured to perform one or more of the processes described herein. Any of the systems, units, computing devices, and/or other components described herein may be implemented by computing device 2000.

As shown in FIG. 20, computing device 2000 may include a communication interface 2002, a processor 2004, a storage device 2006, and an input/output ("I/O") module 2008 communicatively connected one to another via a communication infrastructure 2010. While an exemplary computing device 2000 is shown in FIG. 20, the components illustrated in FIG. 20 are not intended to be limiting. Additional or alternative components may be used in other embodiments. Components of computing device 2000 shown in FIG. 20 will now be described in additional detail.

Communication interface 2002 may be configured to communicate with one or more computing devices. Examples of communication interface 2002 include, without limitation, a wired network interface (such as a network interface card), a wireless network interface (such as a wireless network interface card), a modem, an audio/video connection, and any other suitable interface.

Processor 2004 generally represents any type or form of processing unit capable of processing data and/or interpreting, executing, and/or directing execution of one or more of the instructions, processes, and/or operations described herein. Processor 2004 may perform operations by executing computer-executable instructions 2012 (e.g., an application, software, code, and/or other executable data instance) stored in storage device 2006.

Storage device 2006 may include one or more data storage media, devices, or configurations and may employ any type, form, and combination of data storage media and/or device. For example, storage device 2006 may include, but is not limited to, any combination of the non-volatile media and/or volatile media described herein. Electronic data, including data described herein, may be temporarily and/or permanently stored in storage device 2006. For example, data representative of computer-executable instructions 2012 configured to direct processor 2004 to perform any of the operations described herein may be stored within storage device 2006. In some examples, data may be arranged in one or more databases residing within storage device 2006.

I/O module 2008 may include one or more I/O modules configured to receive user input and provide user output. I/O module 2008 may include any hardware, firmware, software, or combination thereof supportive of input and output capabilities. For example, I/O module 2008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2008 is configured to provide graphical data to a display for presentation to a user. The graphical data may be representative of one or more graphical user interfaces and/or any other graphical content as may serve a particular implementation.

Figure 21:
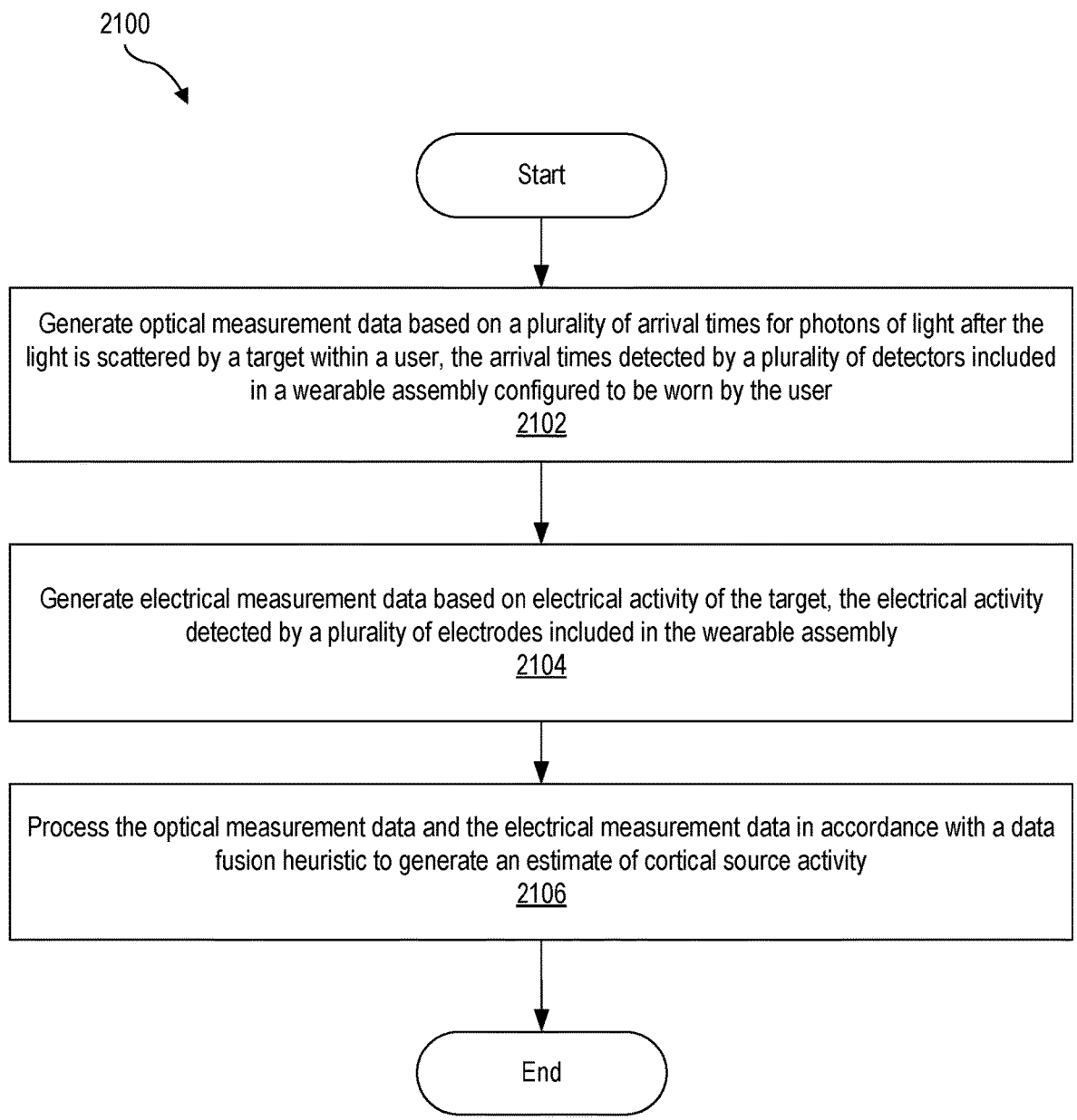
FIG. 21 illustrates an exemplary method.

FIG. 21 illustrates an exemplary method 2100 that may be performed by processing unit 1204 and/or any implementation thereof. While FIG. 21 illustrates exemplary operations according to one embodiment, other embodiments may omit, add to, reorder, and/or modify any of the operations shown in FIG. 21. Each of the operations shown in FIG. 21 may be performed in any of the ways described herein.

At operation 2102, a processing unit generates optical measurement data based on a plurality of arrival times for photons of light after the light is scattered by a target within a user, the arrival times detected by a plurality of detectors included in a wearable assembly configured to be worn by the user.

At operation 2104, the processing unit generates electrical measurement data based on electrical activity of the target, the electrical activity detected by a plurality of electrodes included in the wearable assembly.

At operation 2106, the processing unit processes the optical measurement data and the electrical measurement data in accordance with a data fusion heuristic to generate an estimate of cortical source activity.

An illustrative multimodal measurement system includes a wearable assembly configured to be worn by a user and comprising: a plurality of light sources each configured to emit light directed at a target within the user, a plurality of detectors configured to detect arrival times for photons of the light after the light is scattered by the target, and a plurality of electrodes configured to be external to the user and detect electrical activity of the target.

Another illustrative multimodal measurement system includes a wearable assembly configured to be worn by a user and comprising: a light source configured to emit light directed at a target within the user, a detector configured to detect arrival times for photons of the light after the light is scattered by the target, and an electrode configured to be external to the user and detect electrical activity of the target.

Another illustrative multimodal measurement system includes a headgear configured to be worn on a head of a user and having a plurality of slots; a first module configured to be located in a first slot of the plurality of slots and comprising: a first light source configured to emit light directed at a target within the head of the user, and a first set of detectors configured to detect arrival times for photons of the light emitted by the first light source; a second module configured to be located in a second slot of the plurality of slots and comprising: a second light source configured to emit light directed at the target within the head of the user, and a second set of detectors configured to detect arrival times for photons of the light emitted by the second light source; and a plurality of electrodes on one or more of the headgear, the first module, or the second module and configured to detect electrical activity of the target.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A multimodal measurement system comprising:
   a wearable assembly configured to be worn by a user and comprising:
   a plurality of light sources each configured to emit light directed at a target within the user,
   a plurality of detectors configured to detect arrival times for photons of the light after the light is scattered by the target,
   a plurality of electrodes configured to be external to the user and detect electrical activity of the target,
   a first slot surrounded by a first wall,
   a second slot surrounded by a second wall,
   a third slot surrounded by a third wall,
   a first module configured to be removably inserted into the first slot, the first module comprising a first light source included in the plurality of light sources and a first set of detectors included in the plurality of detectors,
   a second module configured to be removably inserted into the second slot, the second module physically distinct from the first module and comprising a second light source included in the plurality of light sources and a second set of detectors included in the plurality of detectors, and
   a third module configured to be removably inserted into the third slot, the third module physically distinct from the first and second modules and comprising a third light source included in the plurality of light sources and a third set of detectors included in the plurality of detectors,
   wherein the first module comprises:
   a housing,
   a printed circuit board (PCB) housed within the housing, and
   a light guide assembly that implements the first light source, the light guide assembly comprising:
   a lower light guide portion housed within the housing and having a proximal end attached to the PCB,
   a conductive spring member housed within the housing and comprising a coil positioned around an external surface of the lower light guide portion, and
   a conductive upper light guide portion connected to the lower light guide portion and configured to protrude from an upper surface of the housing and be in contact with a surface of a body of the user, the conductive upper light guide portion conductively coupled to circuitry on the PCB by way of the conductive spring member;
   wherein the conductive upper light guide portion functions as an electrode included in the plurality of electrodes.

2. The multimodal measurement of claim 1, wherein the first and second sets of detectors each include at least two detectors.

3. The multimodal measurement system of claim 1, wherein:
   the first and second light sources are both configured to emit light having a first wavelength;
   the first module further comprises a fourth light source configured to emit light having a second wavelength different than the first wavelength; and
   the second module further comprises a fifth light source configured to emit light having the second wavelength.

4. The multimodal measurement system of claim 1, wherein the plurality of electrodes further comprises an electrode on a surface of the first module and an electrode on a surface of the second module.

5. The multimodal measurement system of claim 1, wherein the conductive spring member is further configured to bias a distal end of the conductive upper light guide portion towards the surface of the body of the user.

6. The multimodal measurement system of claim 1, wherein the plurality of electrodes are conductively coupled to one another to create a single channel.

7. The multimodal measurement system of claim 1, wherein at least one electrode of the plurality of electrodes is conductively isolated from a remaining number of electrodes of the plurality of electrodes to create at least two channels.

8. The multimodal measurement system of claim 1, wherein the electrical activity comprises electroencephalogram (EEG) activity.

9. The multimodal measurement system of claim 1, further comprising a processing unit configured to generate optical measurement data based on the arrival times detected by the plurality of detectors and electrical measurement data based on the electrical activity detected by the plurality of electrodes.

10. The multimodal measurement system of claim 9, wherein the optical measurement data comprises time-domain functional near infrared spectroscopy (fNIRS) data and the electrical measurement data comprises electroencephalogram (EEG) data.

11. The multimodal measurement system of claim 9, wherein the processing unit is further configured to process the optical measurement data and the electrical measurement data in accordance with a data fusion heuristic to generate an estimate of cortical source activity.

12. The multimodal measurement system of claim 11, wherein the generating of the estimate of the cortical source activity is performed in real-time while the plurality of detectors are detecting the arrival times and the plurality of electrodes are detecting the electrical activity.

13. The multimodal measurement system of claim 9, wherein the processing unit is included in the wearable assembly.

14. The multimodal measurement system of claim 9, wherein the processing unit is not included in the wearable assembly.

15. The multimodal measurement system of claim 1, wherein each detector in the plurality of detectors comprises:
- a photodetector configured to generate a photodetector output pulse in response to detecting a photon of the light; and
- a time-to-digital converter configured to record a timestamp symbol in response to an occurrence of the photodetector output pulse, the timestamp symbol representative of an arrival time for the photon.

16. The multimodal measurement system of claim 1, wherein the target is a brain of the user.

17. The multimodal measurement system of claim 1, wherein the plurality of electrodes are configured to be in contact with the surface of the body of the user while the wearable assembly is worn by the user.

18. The multimodal measurement system of claim 1, wherein the wearable assembly comprises headgear configured to be worn on a head of the user.

* * * * *